(12) United States Patent
Tesar

(10) Patent No.: US 9,877,654 B2
(45) Date of Patent: Jan. 30, 2018

(54) NEAR INFRARED IMAGING

(75) Inventor: John C. Tesar, Tucson, AZ (US)

(73) Assignee: NOVADAQ TECHNOLOGIES INC., Mississauga (CA)

( * ) Notice: Subject to any disclaimer, the term of this patent is extended or adjusted under 35 U.S.C. 154(b) by 0 days.

(21) Appl. No.: 13/585,824

(22) Filed: Aug. 14, 2012

(65) Prior Publication Data

US 2013/0184591 A1 Jul. 18, 2013

Related U.S. Application Data

(63) Continuation of application No. 12/278,740, filed as application No. PCT/US2007/061810 on Feb. 7, 2007, now abandoned.

(60) Provisional application No. 60/771,288, filed on Feb. 7, 2006, provisional application No. 60/793,979, filed
(Continued)

(51) Int. Cl.
| A61B 5/00 | (2006.01) |
| C03C 17/34 | (2006.01) |
| G02B 5/04 | (2006.01) |
| G02B 23/24 | (2006.01) |
| G02B 27/10 | (2006.01) |
| G02B 27/14 | (2006.01) |
| H04N 5/225 | (2006.01) |
| H04N 5/33 | (2006.01) |

(Continued)

(52) U.S. Cl.
CPC .......... *A61B 5/0075* (2013.01); *A61B 1/0661* (2013.01); *A61B 1/07* (2013.01); *C03C 17/3417* (2013.01); *C03C 17/3452* (2013.01); *G02B 5/04* (2013.01); *G02B 23/2453* (2013.01); *G02B 27/1013* (2013.01); *G02B 27/142* (2013.01); *G02B 27/145* (2013.01); *H04N 5/2256* (2013.01); *H04N 5/33* (2013.01); *H04N 2005/2255* (2013.01)

(58) Field of Classification Search
CPC ... A61B 5/0075; A61B 5/0084; A61B 5/0086; A61B 1/0661; A61B 1/07
USPC .................................................. 600/473–476
See application file for complete search history.

(56) References Cited

U.S. PATENT DOCUMENTS

| 3,215,029 A | 11/1965 | Woodcock |
| 3,257,902 A | 6/1966 | Hopkins |
| 3,971,068 A | 7/1976 | Gerhardt et al. |

(Continued)

FOREIGN PATENT DOCUMENTS

| CA | 2 404 600 A1 | 10/2001 |
| CN | 200987662 Y | 12/2007 |

(Continued)

OTHER PUBLICATIONS

Bennett, Jean M. et al, Infrared Reflectance and Emittance of Silver and Gold Evaporated in Ultrahigh Vacuum, Feb. 1965, Applied Optics, vol. 4, No. 2, pp. 221-224.*

(Continued)

*Primary Examiner* — Rochelle Turchen
(74) *Attorney, Agent, or Firm* — Morrison & Foerster LLP

(57) ABSTRACT

Endoscopes and wands, useful for near infrared imaging, particularly for medical purposes, have transmitting members that transmit between about 95% and 99.5% of the energy at a wavelength within the infrared spectrum. The wands and endoscopes have at least one channel for transmitting and receiving light in the visible spectrum and at least one channel for transmitting and receiving light in the infrared spectrum.

11 Claims, 12 Drawing Sheets

Related U.S. Application Data on Apr. 20, 2006, provisional application No. 60/828,627, filed on Oct. 6, 2006.

(51) Int. Cl.
  *A61B 1/06* (2006.01)
  *A61B 1/07* (2006.01)

(56) References Cited

U.S. PATENT DOCUMENTS

| | | |
|---|---|---|
| 4,037,866 A | 7/1977 | Price |
| 4,066,330 A | 1/1978 | Jones |
| 4,115,812 A | 9/1978 | Akatsu |
| 4,149,190 A | 4/1979 | Wessler et al. |
| 4,200,801 A | 4/1980 | Schuresko |
| 4,318,395 A | 3/1982 | Tawara |
| 4,355,325 A | 10/1982 | Nakamura et al. |
| 4,378,571 A | 3/1983 | Handy |
| 4,449,535 A | 5/1984 | Renault |
| 4,471,766 A | 9/1984 | Terayama |
| 4,532,918 A | 8/1985 | Wheeler |
| 4,556,057 A | 12/1985 | Hiruma et al. |
| 4,611,888 A | 9/1986 | Prenovitz et al. |
| 4,638,365 A | 1/1987 | Kato |
| 4,655,557 A | 4/1987 | Takahashi |
| 4,660,982 A | 4/1987 | Okada |
| 4,768,513 A | 9/1988 | Suzuki |
| 4,786,813 A | 11/1988 | Svanberg et al. |
| 4,821,117 A | 4/1989 | Sekiguchi |
| 4,837,625 A | 6/1989 | Douziech et al. |
| 4,856,495 A | 8/1989 | Tohjoh et al. |
| 4,895,145 A | 1/1990 | Joffe |
| 4,917,457 A | 4/1990 | Iizuka |
| 4,930,516 A | 6/1990 | Alfano et al. |
| 4,951,135 A | 8/1990 | Sasagawa et al. |
| 4,954,897 A | 9/1990 | Ejima et al. |
| 4,974,936 A | 12/1990 | Ams et al. |
| 5,001,556 A | 3/1991 | Nakamura et al. |
| 5,005,960 A | 4/1991 | Heimbeck |
| 5,007,408 A | 4/1991 | Ieoka |
| 5,034,888 A | 7/1991 | Uehara et al. |
| 5,134,662 A | 7/1992 | Bacus et al. |
| 5,142,410 A | 8/1992 | Ono et al. |
| 5,165,079 A | 11/1992 | Schulz-Hennig |
| 5,205,280 A | 4/1993 | Dennison, Jr. et al. |
| 5,214,503 A | 5/1993 | Chiu et al. |
| 5,225,883 A | 7/1993 | Carter et al. |
| 5,255,087 A | 10/1993 | Nakamura et al. |
| 5,278,642 A | 1/1994 | Danna et al. |
| 5,305,759 A | 4/1994 | Kaneko et al. |
| 5,334,191 A * | 8/1994 | Poppas ............... A61B 18/22 606/10 |
| 5,365,057 A | 11/1994 | Morley et al. |
| 5,371,355 A | 12/1994 | Wodecki |
| 5,377,686 A | 1/1995 | O'Rourke et al. |
| 5,379,756 A | 1/1995 | Pileski et al. |
| 5,408,263 A | 4/1995 | Kikuchi et al. |
| 5,410,363 A | 4/1995 | Capen et al. |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,424,841 A | 6/1995 | Van Gelder et al. |
| 5,430,476 A | 7/1995 | Hafele et al. |
| 5,460,166 A | 10/1995 | Yabe et al. |
| 5,485,203 A | 1/1996 | Nakamura et al. |
| 5,490,015 A | 2/1996 | Umeyama et al. |
| 5,507,287 A | 4/1996 | Palcic et al. |
| 5,536,236 A | 7/1996 | Yabe et al. |
| 5,576,882 A | 11/1996 | Kanamori |
| 5,585,846 A | 12/1996 | Kim |
| 5,590,660 A | 1/1997 | MacAulay et al. |
| 5,596,654 A | 1/1997 | Tanaka |
| 5,646,680 A | 7/1997 | Yajima |
| 5,647,368 A | 7/1997 | Zeng et al. |
| 5,647,840 A | 7/1997 | D'Amelio et al. |
| 5,667,472 A | 9/1997 | Finn et al. |
| 5,684,629 A | 11/1997 | Leiner |
| 5,695,049 A | 12/1997 | Bauman |
| 5,697,373 A | 12/1997 | Richards-Kortum et al. |
| 5,697,888 A | 12/1997 | Kobayashi et al. |
| 5,713,364 A | 2/1998 | DeBaryshe et al. |
| 5,722,962 A | 3/1998 | Garcia |
| 5,749,830 A | 5/1998 | Kaneko et al. |
| 5,772,355 A | 6/1998 | Ross et al. |
| 5,772,580 A | 6/1998 | Utsui et al. |
| 5,827,190 A | 10/1998 | Palcic et al. |
| 5,833,617 A | 11/1998 | Hayashi |
| 5,852,498 A | 12/1998 | Youvan et al. |
| 5,891,016 A | 4/1999 | Utsui et al. |
| 5,892,625 A | 4/1999 | Heimer |
| 5,897,269 A | 4/1999 | Ross et al. |
| 5,910,816 A | 6/1999 | Fontenot et al. |
| 5,941,815 A | 8/1999 | Chang |
| 5,952,768 A | 9/1999 | Strok et al. |
| 5,971,918 A | 10/1999 | Zanger |
| 5,976,146 A | 11/1999 | Ogawa et al. |
| 5,984,861 A | 11/1999 | Crowley |
| 5,986,271 A | 11/1999 | Lazarev et al. |
| 5,986,642 A | 11/1999 | Lazarev et al. |
| 5,990,996 A | 11/1999 | Sharp |
| 5,999,240 A | 12/1999 | Sharp et al. |
| 6,002,137 A | 12/1999 | Hayashi |
| 6,004,263 A | 12/1999 | Nakaichi et al. |
| 6,008,889 A | 12/1999 | Zeng et al. |
| 6,021,344 A | 2/2000 | Lui et al. |
| 6,028,622 A | 2/2000 | Suzuki |
| 6,030,339 A | 2/2000 | Tatsuno et al. |
| 6,059,719 A | 5/2000 | Yamamoto et al. |
| 6,059,720 A | 5/2000 | Furusawa et al. |
| 6,061,591 A | 5/2000 | Freitag et al. |
| 6,069,689 A | 5/2000 | Zeng et al. |
| 6,070,096 A | 5/2000 | Hayashi |
| 6,095,982 A | 8/2000 | Richards-Kortum et al. |
| 6,099,466 A | 8/2000 | Sano et al. |
| 6,110,103 A | 8/2000 | Donofrio |
| 6,110,106 A | 8/2000 | MacKinnon et al. |
| 6,120,435 A | 9/2000 | Eino |
| 6,148,227 A | 11/2000 | Wagnieres et al. |
| 6,161,035 A | 12/2000 | Furusawa |
| 6,166,496 A | 12/2000 | Lys et al. |
| 6,192,267 B1 | 2/2001 | Scherninski et al. |
| 6,212,425 B1 | 4/2001 | Irion et al. |
| 6,258,576 B1 | 7/2001 | Richards-Kortum et al. |
| 6,280,378 B1 | 8/2001 | Kazuhiro et al. |
| 6,293,911 B1 | 9/2001 | Imaizumi et al. |
| 6,332,092 B1 | 12/2001 | Deckert et al. |
| 6,347,010 B1 | 2/2002 | Chen et al. |
| 6,351,663 B1 | 2/2002 | Flower et al. |
| 6,364,829 B1 | 4/2002 | Fulghum |
| 6,364,831 B1 | 4/2002 | Crowley |
| 6,388,702 B1 | 5/2002 | Konomura et al. |
| 6,419,628 B1 | 7/2002 | Rudischhauser et al. |
| 6,422,994 B1 | 7/2002 | Kaneko et al. |
| 6,433,102 B1 | 8/2002 | Suzuki et al. |
| 6,443,976 B1 | 9/2002 | Flower et al. |
| 6,461,330 B1 | 10/2002 | Miyagi |
| 6,490,085 B1 | 12/2002 | Zobel |
| 6,526,213 B1 | 2/2003 | Ilenda et al. |
| 6,527,709 B2 | 3/2003 | Matsumoto |
| 6,529,768 B1 | 3/2003 | Hakamata |
| 6,537,211 B1 | 3/2003 | Wang et al. |
| 6,544,102 B2 | 4/2003 | Schafer et al. |
| 6,571,119 B2 | 5/2003 | Hayashi |
| 6,603,552 B1 | 8/2003 | Cline et al. |
| 6,639,664 B2 | 10/2003 | Haan et al. |
| 6,772,003 B2 | 8/2004 | Kaneko et al. |
| 6,773,392 B2 | 8/2004 | Kikuchi et al. |
| 6,786,865 B2 | 9/2004 | Dhindsa |
| 6,821,245 B2 | 11/2004 | Cline et al. |
| 6,853,485 B2 | 2/2005 | Hoogland |
| 6,898,458 B2 | 5/2005 | Zeng et al. |
| 6,899,675 B2 | 5/2005 | Cline et al. |
| 6,907,527 B1 | 6/2005 | Wu |
| 6,911,005 B2 | 6/2005 | Ouchi et al. |

(56) References Cited

U.S. PATENT DOCUMENTS

| | | |
|---|---|---|
| 6,915,154 B1 | 7/2005 | Docherty et al. |
| 6,944,493 B2 | 9/2005 | Alam et al. |
| 6,958,035 B2 | 10/2005 | Friedman et al. |
| 6,960,165 B2 | 11/2005 | Ueno et al. |
| 7,033,314 B2 | 4/2006 | Kamrava et al. |
| 7,043,291 B2 | 5/2006 | Sendai |
| 7,235,045 B2 | 6/2007 | Wang et al. |
| 7,236,815 B2 | 6/2007 | Richards-Kortum et al. |
| 7,324,674 B2 | 1/2008 | Ozawa et al. |
| 7,341,557 B2 | 3/2008 | Cline et al. |
| 7,364,574 B2 | 4/2008 | Flower |
| 7,385,772 B2 | 6/2008 | Forkey et al. |
| 7,704,206 B2 | 4/2010 | Suzuki et al. |
| 7,722,534 B2 | 5/2010 | Cline et al. |
| 7,724,430 B2 | 5/2010 | Kasai |
| 7,733,583 B2 | 6/2010 | Fujiwara |
| 7,733,584 B2 | 6/2010 | Kazakevich |
| 7,798,955 B2 | 9/2010 | Ishihara et al. |
| 7,862,504 B2 | 1/2011 | Kura et al. |
| 7,918,559 B2 | 4/2011 | Tesar |
| 8,408,269 B2 | 4/2013 | Fengler et al. |
| 8,506,555 B2 | 8/2013 | Ruiz Morales |
| 8,630,698 B2 | 1/2014 | Fengler et al. |
| 8,780,445 B2 | 7/2014 | Inoue |
| 8,961,403 B2 | 2/2015 | Cline et al. |
| 9,241,615 B2 | 1/2016 | Yoshida et al. |
| 9,386,909 B2 | 7/2016 | Fengler et al. |
| 2001/0016679 A1 | 8/2001 | Futatsugi et al. |
| 2002/0035330 A1 | 3/2002 | Cline et al. |
| 2002/0057501 A1 | 5/2002 | Lei |
| 2002/0072736 A1 | 6/2002 | Tierney et al. |
| 2002/0087047 A1* | 7/2002 | Remijan ............ A61B 1/00142 600/109 |
| 2002/0103439 A1 | 8/2002 | Zeng et al. |
| 2002/0138008 A1 | 9/2002 | Tsujita et al. |
| 2002/0161283 A1 | 10/2002 | Sendai |
| 2002/0161284 A1 | 10/2002 | Tanaka |
| 2002/0175993 A1 | 11/2002 | Ueno et al. |
| 2002/0177778 A1 | 11/2002 | Averback et al. |
| 2002/0186478 A1 | 12/2002 | Watanabe et al. |
| 2003/0002036 A1 | 1/2003 | Haan et al. |
| 2003/0042493 A1 | 3/2003 | Kazakevich |
| 2003/0153811 A1 | 8/2003 | Muckner |
| 2003/0219383 A1 | 11/2003 | Weissleder et al. |
| 2003/0229270 A1 | 12/2003 | Suzuki et al. |
| 2004/0010183 A1 | 1/2004 | Dhindsa |
| 2004/0021859 A1 | 2/2004 | Cunningham |
| 2004/0037454 A1 | 2/2004 | Ozawa et al. |
| 2004/0046865 A1 | 3/2004 | Ueno et al. |
| 2004/0054255 A1 | 3/2004 | Pilgrim et al. |
| 2004/0125445 A1 | 7/2004 | Hoogland |
| 2004/0133073 A1 | 7/2004 | Berci et al. |
| 2004/0142485 A1 | 7/2004 | Flower et al. |
| 2004/0143162 A1 | 7/2004 | Krattiger et al. |
| 2004/0148141 A1 | 7/2004 | Tsujita et al. |
| 2004/0156124 A1 | 8/2004 | Okada |
| 2004/0186383 A1* | 9/2004 | Rava et al. ............... 600/473 |
| 2004/0204671 A1 | 10/2004 | Stubbs et al. |
| 2004/0218115 A1 | 11/2004 | Kawana et al. |
| 2005/0027166 A1 | 2/2005 | Matsumoto et al. |
| 2005/0075575 A1 | 4/2005 | Vo-Dinh |
| 2005/0096505 A1 | 5/2005 | Imaizumi et al. |
| 2005/0143627 A1 | 6/2005 | Cline et al. |
| 2005/0152027 A1 | 7/2005 | Armstrong et al. |
| 2005/0154319 A1 | 7/2005 | Cline et al. |
| 2005/0182291 A1 | 8/2005 | Hirata |
| 2005/0256373 A1 | 11/2005 | Bar-Or et al. |
| 2005/0267331 A1 | 12/2005 | Secrest et al. |
| 2005/0275057 A1 | 12/2005 | Breen et al. |
| 2006/0017913 A1 | 1/2006 | Kawamata et al. |
| 2006/0089554 A1 | 4/2006 | Ishihara et al. |
| 2006/0146322 A1 | 7/2006 | Komachi et al. |
| 2006/0211915 A1 | 9/2006 | Takeuchi et al. |
| 2006/0217594 A1 | 9/2006 | Ferguson |
| 2006/0239921 A1 | 10/2006 | Mangat et al. |
| 2006/0241496 A1 | 10/2006 | Fengler et al. |
| 2006/0258910 A1 | 11/2006 | Stefanchik et al. |
| 2008/0021274 A1 | 1/2008 | Bayer et al. |
| 2008/0081948 A1 | 4/2008 | Weisenburgh et al. |
| 2008/0239070 A1 | 10/2008 | Westwick et al. |
| 2008/0273247 A1 | 11/2008 | Kazakevich |
| 2009/0012361 A1 | 1/2009 | MacKinnon et al. |
| 2009/0209813 A1 | 8/2009 | Lubowski et al. |
| 2009/0290236 A1 | 11/2009 | Wang et al. |
| 2009/0303317 A1 | 12/2009 | Tesar |
| 2010/0081988 A1 | 4/2010 | Kahle et al. |
| 2010/0125164 A1 | 5/2010 | LaBombard |
| 2010/0168588 A1 | 7/2010 | Matsumoto et al. |
| 2010/0198010 A1 | 8/2010 | Cline et al. |
| 2010/0277817 A1 | 11/2010 | Durell |
| 2011/0230719 A1 | 9/2011 | Katakura et al. |
| 2011/0249323 A1 | 10/2011 | Tesar et al. |
| 2012/0316394 A1 | 12/2012 | Yoshida et al. |
| 2013/0184591 A1 | 7/2013 | Tesar |
| 2013/0194667 A1 | 8/2013 | Inoue |
| 2014/0187859 A1 | 7/2014 | Leeuw et al. |
| 2014/0194687 A1 | 7/2014 | Fengler et al. |
| 2014/0343362 A1 | 11/2014 | Tesar |
| 2015/0230698 A1 | 8/2015 | Cline et al. |
| 2016/0270640 A1 | 9/2016 | Fengler et al. |

FOREIGN PATENT DOCUMENTS

| | | |
|---|---|---|
| CN | 101115995 A | 1/2008 |
| CN | 201048936 Y | 4/2008 |
| CN | 201085616 Y | 7/2008 |
| CN | 102004309 A | 4/2011 |
| CN | 103091829 A | 5/2013 |
| DE | 195 35 114 A1 | 3/1996 |
| DE | 196 08 027 A1 | 9/1996 |
| EP | 0 512 965 A1 | 11/1992 |
| EP | 0 672 379 A1 | 9/1995 |
| EP | 0 774 685 A2 | 5/1997 |
| EP | 0 774 865 A2 | 5/1997 |
| EP | 0 792 618 A1 | 9/1997 |
| EP | 1 232 764 A1 | 8/2002 |
| EP | 1 374 755 A1 | 1/2004 |
| EP | 1 883 337 A1 | 2/2008 |
| EP | 2 051 603 A1 | 4/2009 |
| EP | 2106739 A2 | 10/2009 |
| FR | 2 671 405 A1 | 7/1992 |
| JP | S60-246733 A | 12/1985 |
| JP | S61-159936 A | 7/1986 |
| JP | H01-135349 A | 5/1989 |
| JP | H02-272513 A | 11/1990 |
| JP | 03-97439 A | 4/1991 |
| JP | 03-97441 A | 4/1991 |
| JP | 03-97442 A | 4/1991 |
| JP | H03-136630 A | 6/1991 |
| JP | H05-005101 U | 1/1993 |
| JP | H05-115435 A | 5/1993 |
| JP | 6-63164 A | 3/1994 |
| JP | 06-125911 A | 5/1994 |
| JP | H06-068702 U | 9/1994 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | H07-184832 A | 7/1995 |
| JP | H07-204156 A | 8/1995 |
| JP | H07-222712 A | 8/1995 |
| JP | H07-250804 A | 10/1995 |
| JP | H07-250812 A | 10/1995 |
| JP | H07-327913 A | 12/1995 |
| JP | H08-056894 A | 3/1996 |
| JP | H08-094928 A | 4/1996 |
| JP | H08-126605 A | 5/1996 |
| JP | 08-140928 A | 6/1996 |
| JP | 08-140929 A | 6/1996 |
| JP | H08-168465 A | 7/1996 |
| JP | H08-224208 A | 9/1996 |
| JP | H08-224209 A | 9/1996 |
| JP | H08-224210 A | 9/1996 |

(56) References Cited

FOREIGN PATENT DOCUMENTS

| | | |
|---|---|---|
| JP | H08-224240 A | 9/1996 |
| JP | H08-228998 A | 9/1996 |
| JP | H08-252218 A | 10/1996 |
| JP | 09-066023 A | 3/1997 |
| JP | 09-070384 A | 3/1997 |
| JP | H10-127563 A | 5/1998 |
| JP | H10-151104 A | 6/1998 |
| JP | H10-192297 A | 7/1998 |
| JP | 10-201707 A2 | 8/1998 |
| JP | 10-225427 A2 | 8/1998 |
| JP | H10-201700 A | 8/1998 |
| JP | H10-225426 A | 8/1998 |
| JP | H10-243915 A | 9/1998 |
| JP | H10-243920 A | 9/1998 |
| JP | H10-262907 A | 10/1998 |
| JP | H10-308114 A | 11/1998 |
| JP | H10-309281 A | 11/1998 |
| JP | H10-309282 A | 11/1998 |
| JP | H10-328129 A | 12/1998 |
| JP | 11-047079 A | 2/1999 |
| JP | 11-089789 A2 | 4/1999 |
| JP | H11-104059 A | 4/1999 |
| JP | H11-104060 A | 4/1999 |
| JP | H11-104061 A | 4/1999 |
| JP | H11-104070 A | 4/1999 |
| JP | H11-113839 A | 4/1999 |
| JP | H11-155812 A | 6/1999 |
| JP | H11-244220 A | 9/1999 |
| JP | H11-322819 A | 12/1999 |
| JP | 2000-504968 A | 4/2000 |
| JP | 2000-245693 A | 9/2000 |
| JP | 2000-287915 A | 10/2000 |
| JP | 2000-354583 A | 12/2000 |
| JP | 2001-212245 A | 8/2001 |
| JP | 2002-244122 A | 8/2002 |
| JP | 2004-024611 A | 1/2004 |
| JP | 2004-057520 A | 2/2004 |
| JP | 2004-094043 A | 3/2004 |
| JP | 2004-163902 A | 6/2004 |
| JP | 2004-247156 A | 9/2004 |
| JP | 2004-292722 A | 10/2004 |
| JP | 2005-010315 A | 1/2005 |
| JP | 2005-058618 A2 | 3/2005 |
| JP | 2005-058619 A2 | 3/2005 |
| JP | 2005-058620 A2 | 3/2005 |
| JP | 2005-080819 A2 | 3/2005 |
| JP | 2005-081079 A2 | 3/2005 |
| JP | 2005-292404 A | 10/2005 |
| JP | 2007-143624 A | 6/2007 |
| JP | 2008-511341 A | 4/2008 |
| JP | 2009-048085 A | 3/2009 |
| JP | 2009-247566 A | 10/2009 |
| JP | 2010-526342 A | 7/2010 |
| JP | 2012-050618 A | 3/2012 |
| JP | 5089168 B2 | 12/2012 |
| RU | 2412800 C2 | 2/2011 |
| WO | WO-1993/04648 A1 | 3/1993 |
| WO | WO-1995/26673 A2 | 10/1995 |
| WO | WO-1998/24360 A1 | 6/1998 |
| WO | WO-1999/01749 A1 | 1/1999 |
| WO | WO-1999/53832 A1 | 10/1999 |
| WO | WO-2000/06013 A1 | 2/2000 |
| WO | WO-2000/42910 A1 | 7/2000 |
| WO | WO-2000/54652 A1 | 9/2000 |
| WO | WO-2002/07587 A2 | 1/2002 |
| WO | WO-2003/059159 A2 | 7/2003 |
| WO | WO-2003/059159 A8 | 7/2003 |
| WO | WO-2005/110196 A1 | 11/2005 |
| WO | WO-2006/116634 A2 | 11/2006 |
| WO | WO-2006/116847 A1 | 11/2006 |
| WO | WO-2006/119349 A2 | 11/2006 |
| WO | WO-2008/011722 A1 | 1/2008 |
| WO | WO-2013/021704 A1 | 2/2013 |
| WO | WO-2014/199236 A2 | 12/2014 |

OTHER PUBLICATIONS

M.E. Arregui et al, Principles of Laparoscopic Surgery, 1996, Springer-Verlag New York, 35 Visualization, pp. 767-794.*
Donald O'Shea et al, Handbook of Optics Fundamentals, Techniques and Design, 1995, McGraw-Hill, Inc., 33 Aberration Curves in Lens Design, pp. 33.1-33.6.*
International Search Report from International Application No. PCT/US07/061810 dated Feb. 26, 2008.
Non-Final Office Action dated Jun. 14, 2011, for U.S. Appl. No. 12/278,740, filed Dec. 10, 2008; 15 pages.
Final Office Action dated Feb. 14, 2012, for U.S. Appl. No. 12/278,740, filed Dec. 10, 2008; 6 pages.
Orfanidis, S. J. (Jun. 21, 2004) "Multilayer Structures," Chapt 5 in Electromagnetic Waves and Antennas, published by Sophocoles; <http://www.ece.rutgers.edu/~orfanidi/ewa>, 25 pages.
Alfano, R.R. et al. (Oct. 1987). "Fluorescence Spectra From Cancerous and Normal Human Breast and Lung Tissues," *IEEE Journal of Quantum Electronics* QE-23(10):1806-1811.
Andersson-Engels, S. et al. (1989). "Tissue Diagnostics Using Laser-Induced Fluorescence," *Ber. Bunsenges Physical Chemistry* 93:335-342.
Bhunchet, E. et al. (2002). "Fluorescein Electronic Endoscopy: A Novel Method for Detection of Early Stage Gastric Cancer Not Evident to Routine Endoscopy," *Gastrointestinal Endoscopy* 55(4):562-571.
Hung, J. et al. (1991). "Autofluorescence of Normal and Malignant Bronchial Tissue," *Lasers in Surgery and Medicine* 11:99-105.
Schott AG's Catalog for Optical Glasses. (Feb. 2016). "As the source of the SCHOTT Table." (No Translation).
Sherwinter, D.A. (Aug. 2013, e-published on Oct. 11, 2012). "A Novel Adaptor Converts a Laparoscope Into a high-Definition Rigid Sigmoidoscope," *Surgical Innovation* 20(4):411-413.
Tomkinson, T.H. et al. (Dec. 1, 1996). "Rigid Endoscopic Relay Systems: A Comparative Study," *Applied Optics* 35:6674-6683.
Canadian Office Action dated Dec. 30, 2015, for Canadian Patent Application No. 2,896,267, filed on Sep. 22, 2014, four pages.
Canadian Office Action dated Nov. 29, 2016, for Canadian Patent Application No. 2,896,267, filed on Sep. 22, 2014, four pages.
Canadian Office Action dated Jan. 4, 2017 for Canadian Application No. 2,911,861, filed on May 15, 2014, four pages.
Chinese First Office Action dated Aug. 3, 2016 for Chinese Application No. 201380073686.0, filed on Dec. 24, 2013, eight pages.
Chinese First Office Action dated Nov. 2, 2016 for Chinese Application Number 201480027537.5, filed on May 15, 2014, 17 pages.
Chinese Second Office Action dated Mar. 9, 2017, for Chinese Application No. 201380073686.0, filed on Dec. 24, 2013, nineteen pages.
European Communication pursuant to Rules 70(2) and 70a(2) EPC dated Aug. 4, 2016 for European Application No. 13871081.9, filed on Dec. 24, 2013, one page.
European Extended Search Report dated Dec. 16, 2016 for EP Application No. 14810752.7, filed on Sep. 8, 2016, eight pages.
European Office Action dated Nov. 19, 2015, for EP Application No. 07 785 001.4, filed on Jul. 30, 2007, four pages.
European Supplementary Search Report dated Oct. 9, 2013, for European Patent Application No. 06721854.5, filed on May 4, 2005, six pages.
European Supplementary Search Report dated Jan. 24, 2012 for EP Application No. 07 785 001.4, filed on Jul. 30, 2007, seven pages.
Extended European Search Report dated Jul. 18, 2016 for European Application No. 13871081.9, filed on Dec. 24, 2013, seven pages.
International Preliminary Report on Patentability dated Feb. 3, 2009, for International Application No. PCT/CA2007/001335, filed on Jul. 30, 2007, five pages.
International Preliminary Report on Patentability dated Nov. 6, 2007, for International Application No. PCT/CA2006/000669, filed on Apr. 27, 2006, nine pages.
International Search Report and Written Opinion dated Sep. 22, 2014, for International Application No. PCT/IB2013/003243, filed on Dec. 24, 2013, six pages.

(56) References Cited

OTHER PUBLICATIONS

International Search Report dated Aug. 3, 2006, for International Application No. PCT/CA2006/000669, filed on Apr. 27, 2006, three pages.
International Search Report dated Dec. 7, 2007, for International Application No. PCT/CA2007/001335, filed on Jul. 30, 2007, two pages.
International Search Report dated Jan. 21, 2002, for International Application No. PCT/US2001/022198, filed on Jul. 13, 2001, three pages.
Japanese Final Office Action dated Aug. 2, 2013, for Japanese Patent Application No. 2008-509275, filed on Apr. 27, 2006, four pages.
Japanese Office Action dated Feb. 17, 2012, for Japanese Patent Application No. 2008-509275, filed on Apr. 27, 2006, six pages.
Japanese Office Action dated Jul. 4, 2016, for Japanese Patent Application No. 2015-550160, filed on Dec. 24, 2013, ten pages.
Japanese Office Action dated Nov. 11, 2011, for Japanese Patent Application No. 2009-521077, filed on Jul. 30, 2007, four pages.
Japanese Office Action dated Dec. 5, 2016 for Japanese Patent Application No. 2016-513460, filed on May 15, 2014, nine pages.
Japanese Office Action dated Mar. 3, 2017 for Japanese Patent Application No. 2015-550160, filed on Jun. 24, 2015, nine pages.
Japanese Office Action dated Sep. 14, 2012, for Japanese Patent Application No. 2008-509275, filed on Apr. 27, 2006, seven pages.
Japanese Office Action dated Sep. 19, 2014, for Japanese Patent Application No. 2013-246636, filed on Apr. 27, 2006, six pages.
Korean Final Office Action dated Feb. 13, 2017, for Korean Patent Application No. 2015-7019659, filed on Jul. 20, 2015, twelve pages.
Korean Office Action dated Jan. 6, 2017 for Korean Patent Application No. 10- 2015-7035138, filed on Dec. 10, 2015, ten pages.
Korean Office Action dated Jul. 15, 2016 for Korean Patent Application No. 10-2015-7019659, filed Dec. on 24, 2013, twelve pages.
Korean Notice of Allowance dated Aug. 14, 2017, for Korean Application No. 10-2015-7035138, filed on Dec. 10, 2015, three pages.
Russian Office Action dated Dec. 29, 2016, for Russian Application No. 2015124802, filed on Dec. 24, 2013, thirteen pages.
U.S. Final Office Action dated Aug. 8, 2016 for U.S. Appl. No. 14/278,833, filed May 15, 2014, seven pages.
U.S. Final Office Action dated Jan. 23, 2017 for U.S. Appl. No. 14/140,370, filed Dec. 24, 2013, twelve pages.
U.S. Final Office Action dated Mar. 3, 2016 for U.S. Appl. No. 14/140,370, filed Dec. 24, 2013, ten pages.
U.S. Final Office Action dated Oct. 6, 2016 for U.S. Appl. No. 14/629,473, filed Feb. 23, 2015, seventeen pages.
U.S. Final Office Action dated Jul. 23, 2008, for U.S. Appl. No. 11/122,267, filed May 4, 2005, six pages.
U.S. Final Office Action dated Jun. 18, 2015, for U.S. Appl. No. 14/154,177, filed Jan. 13, 2014, eight pages.
U.S. Final Office Action dated Jun. 5, 2014, for U.S. Appl. No. 12/761,462, filed Apr. 16, 2010, fourteen pages.
U.S. Final Office Action dated May 11, 2011, for U.S. Appl. No. 11/412,715, filed Apr. 26, 2006, eight pages.
U.S. Final Office Action dated May 19, 2017, for U.S. Appl. No. 14/975,707, filed Dec. 18, 2015, six pages.
U.S. Final Office Action dated Nov. 24, 2009, for U.S. Appl. No. 11/009,965, filed Dec. 10, 2004, fourteen pages.
U.S. Non Final Office Action dated Dec. 31, 2015 for U.S. Appl. No. 14/278,833, filed May 15, 2014, seven pages.
U.S. Non Final Office Action dated Oct. 23, 2015 for U.S. Appl. No. 14/140,370, filed Dec. 24, 2013, eight pages.
U.S. Non-Final Office Action dated Apr. 2, 2009, for U.S. Appl. No. 11/009,965, filed Dec. 10, 2004, thirteen pages.
U.S. Non-Final Office Action dated Aug. 16, 2013, for U.S. Appl. No. 12/761,462, filed Apr. 16, 2010, ten pages.
U.S. Non-Final Office Action dated Aug. 16, 2013, for U.S. Appl. No. 12/761,523, filed Apr. 16, 2010, nine pages.
U.S. Non-Final Office Action dated Dec. 10, 2010, for U.S. Appl. No. 11/412,715, filed Apr. 26, 2006, ten pages.
U.S. Non-Final Office Action dated Dec. 14, 2011, for U.S. Appl. No. 11/412,715, filed Apr. 26, 2006, eight pages.
U.S. Non-Final Office Action dated Jan. 2, 2008, for U.S. Appl. No. 11/122,267, filed May 4, 2005, five pages.
U.S. Non-Final Office Action dated Jan. 20, 2016, for U.S. Appl. No. 14/629,473, filed Feb. 23, 2015, fourteen pages.
U.S. Non-Final Office Action dated Jul. 17, 2003, for U.S. Appl. No. 09/905,642, filed Jul. 13, 2001, six pages.
U.S. Non-Final Office Action dated Jul. 5, 2016, for U.S. Appl. No. 14/975,707, filed Dec. 18, 2015, four pages.
U.S. Non-Final Office Action dated Jun. 1, 2007, for U.S. Appl. No. 10/899,648, filed Jul. 26, 2004, seven pages.
U.S. Non-Final Office Action dated Jun. 20, 2008, for U.S. Appl. No. 11/009,398, filed Dec. 10, 2004, fifteen pages.
U.S. Non-Final Office Action dated Jun. 23, 2010, for U.S. Appl. No. 11/009,965, filed Dec. 10, 2004, fourteen pages.
U.S. Non-Final Office Action dated Jun. 9, 2011, for U.S. Appl. No. 11/830,323, filed Jul. 30, 2007, five pages.
U.S. Non-Final Office Action dated May 18, 2004, for U.S. Appl. No. 10/050,601, filed Jan. 15, 2002, eight pages.
U.S. Non-Final Office Action dated Nov. 23, 2009, for U.S. Appl. No. 11/969,974, filed Jan. 7, 2008, seven pages.
U.S. Non-Final Office Action dated Oct. 23, 2015, for U.S. Appl. No. 14/140,370, filed Dec. 24, 2013, eight pages.
U.S. Non-Final Office Action dated Sep. 27, 2016, for U.S. Appl. No. 14/140,370, filed Dec. 24, 2013, nine pages.
U.S. Non-Final Office Action dated Sep. 12, 2014, for U.S. Appl. No. 14/154,177, filed Jan. 13, 2014, four pages.
U.S. Non-Final Office Action with Restriction Requirement dated Mar. 4, 2011, for U.S. Appl. No. 11/830,323, filed Jul. 30, 2007, nine pages.
U.S. Notice of Allowability dated Jan. 2, 2008, for U.S. Appl. No. 10/899,648, filed Jul. 26, 2004, three pages.
U.S. Notice of Allowance dated Apr. 7, 2004, for U.S. Appl. No. 09/905,642, filed Jul. 13, 2001, six pages.
U.S. Notice of Allowance dated Aug. 26, 2004, for U.S. Appl. No. 10/050,601, filed Jan. 15, 2002, four pages.
U.S. Notice of Allowance dated Aug. 6, 2015, for U.S. Appl. No. 13/853,656, filed Mar. 29, 2013, seven pages.
U.S. Notice of Allowance dated Feb. 25, 2010, for U.S. Appl. No. 11/969,974, filed Jan. 7, 2008, four pages.
U.S. Notice of Allowance dated Jul. 28, 2017, for U.S. Appl. No. 14/629,473, filed Feb. 23, 2015, ten pages.
U.S. Notice of Allowance dated Mar. 28, 2016, for U.S. Appl. No. 13/853,656, filed Mar. 29, 2013, eight pages.
U.S. Notice of Allowance dated Nov. 23, 2015, for U.S. Appl. No. 13/853,656, filed Mar. 29, 2013, seven pages.
U.S. Notice of Allowance dated Oct. 10, 2014, for U.S. Appl. No. 12/761,462, filed Apr. 16, 2010, ten pages.
U.S. Notice of Allowance dated Oct. 5, 2007, for U.S. Appl. No. 10/899,648, filed Jul. 26, 2004, six pages.
U.S. Notice of Allowance dated Jan. 5, 2017, for U.S. Appl. No. 14/278,833, filed May 15, 2014, seven pages.
U.S. Notice of Allowance dated Sep. 10, 2013, for U.S. Appl. No. 11/412,715, filed Apr. 26, 2006, eight pages.
U.S. Notice of Allowance dated Sep. 14, 2012, for U.S. Appl. No. 11/830,323, filed Jul. 30, 2007, eight pages.
U.S. Supplemental Notice of Allowability dated Mar. 10, 2005, for U.S. Appl. No. 10/050,601, filed Jan. 15, 2002, five pages.
Written Opinion of the International Searching Authority dated Aug. 3, 2006, for International Application No. PCT/CA2006/000669, filed on Apr. 27, 2006, eight pages.
Written Opinion of the International Searching Authority dated Dec. 7, 2007, for International Application No. PCT/CA2007/001335, filed on Jul. 30, 2007, four pages.
U.S. Appl. No. 15/073,259, filed Mar. 17, 2016, thirty nine pages. (Copy not attached).

* cited by examiner

NEAR INFRARED IMAGING

RELATED APPLICATIONS

This application is a continuation of U.S. application Ser. No. 12/278,740, having a 371(c) date of Dec. 10, 2008, now abandoned, which is a national stage application of International Application No. PCT/US2007/061810, filed Feb. 7, 2007, which claims priority to U.S. Provisional Application Ser. No. 60/771,288 filed on Feb. 7, 2006, and entitled "Endoscopes and Wands", U.S. Provisional Application Ser. No. 60/793,979 filed on Apr. 20, 2006 and entitled "Endoscopes and wands", and U.S. Provisional Ser. Application No. 60/828,627 filed on Oct. 6, 2006 and entitled "Endoscopes and Wands". Each of these applications is hereby incorporated by reference in its entirety.

TECHNICAL FIELD

This application relates to endoscopes and similar devices.

BACKGROUND OF THE INVENTION

An endoscope or wand viewing apparatus is usually configured in a way that is well suited for illumination and imaging in visible light.

In this background section endoscopes and wand like devices shall be described in terms of their internal working components. In the second portion of the background section the shortcomings of these predicate devices shall be described with respect to their use for laser induced fluorescence imaging.

An endoscope is an opto-mechanical imaging device characterized by the following: an objective lens assembly containing an optional deviating prism assembly, a relay system forming a plurality of intermediate images for the case of a rigid endoscope, an ocular, a camera system containing multiple detectors with a prism assembly directing sections of the electromagnetic spectrum to dedicated sensors, or in the case of chip-on-a-stick endoscope where there are no intermediate images; an objective lens assembly coupled directly to the camera detector which is embedded in the distal most portion of the device. In either case the optical elements are contained in an inner most tube member which is surrounded by other tube members which may include fiber optics for illumination in the annulus formed by two or more of the tubes and may contain other tubes for the passage of instruments and or irrigation.

An objective lens assembly in the distal most portion of the device forms a real image of the scene coincident with the plane of the detector in the case of a chip-on-a-stick endoscope or intraoral camera, or distal most plane of a relay system that is contained within the shaft portion of the endoscope.

In an endoscope with a relay system (the second case above), there are 2 basic forms of relays, those of lenses and those using coherent imaging fibers.

In both examples the role of the relay is to reform the image produced by the objective lens through the length of the shaft by producing intermediate images in the case of a rigid endoscope to a new position where the ocular, in the case of a visual endoscope or camera lens group in the case of a digital or electronic imaging device, may then reform the image originally produced by the objective lens group for the eye or to a camera detector.

The shaft portions of all endoscopes are made to facilitate the insertion of the device into a body cavity or body lumen, that is to say diameter is the dimension being minimized. In the case of a body cavity insertion, the shaft is often rigid and comprised of thin walled stainless steel tubes. This tube within tube construction allows for an innermost tube to contain the optical train and then surrounding tubes can contain fiber optics to transmit illumination to the scene in the form of an annulus. Additional tubes can be contained within the assembly for the introduction of surgical instruments for various purposes.

For the case of an endoscope that utilizes coherent imaging fibers for the relay system the functional concept being optimized in the device is flexibility, and to some degree what is being compromised is resolution, particularly when the diameter of the tip is small. However, large diameter flexible endoscopes often use detectors directly behind the objective lens assembly and are therefore considered "chip-on-a-stick" configurations. These flexible endoscopes often have internal channels, instrument and irrigation channels, to pass forceps, etc. and have internal guide wires and steering mechanisms at the tip controlled by levers at the proximal end of the device.

There is a class of smaller diameter endoscopes utilizing coherent imaging fibers as relays whose shafts have a limited amount of flexibility, and these devices are commonly called semi-flexible. Often configured with a working channel, called a forceps channel, used for instruments and are often used in Urology.

Whether rigid, flexible, or semi-flexible, endoscopes have a proximal eyepiece section for viewing and or coupling to a camera system. An eyepiece is not present on chip-on-a-stick endoscopes or intraoral cameras, often called dental cameras, as the camera is imbedded into the distal portion of the device.

Where eyepieces are used, manufacturers have almost universally adopted a nominal 32 mm eye cup for blocking room light from the physician's view, and this eye cup serves to support the coupling mechanism to the camera. There are some commercial applications of directly coupling the camera and optical assemblies included in the shaft mechanism and or coupling mechanism but this has not found wide acceptance, except in Orthopedics for Arthroscopy. The fear among users has been that if the electronics of the camera fail for some reason then the doctor is left with no means to view within the patient, hence the continuing presence of endoscopes with eyepieces.

The class of endoscopes not utilizing eyepieces is commonly called chip-on-a-stick. The intraoral dental camera shares the lack of eyepiece or ocular, as well. Both instruments send a video signal to a monitor or computer for viewing.

Endoscopes are most commonly fixed focus imaging devices. There is a broad distance from the tip of the device to the subject that is in focus due to the relatively small aperture of the optical system. A small aperture allows only a small amount of light to be imagined for any point in the scene. Should focusing be required it is accomplished by repositioning the optics in the camera module proximal to the endoscope, or in some cases the detector itself is moved.

Such low levels of return signal in the visible spectrum require endoscopes to have large light sources such as xenon, halogen, and metal halide.

In the case of an endoscope, commonly called a chip-on-a-stick which contain a distal most detector (CCD, CMOS, or other sensor), the change in image plane position for a near object of interest versus a far object of interest is usually ameliorated by installing a very small aperture in the objective lens assembly to increase depth of field at the expense of a bright field or higher potential resolution.

This is a distinction between endoscopes and chip-on-a-stick endoscopes regarding focus. Endoscopes with proximal cameras do provide a means for focus even if they themselves are fixed focus. Chip-on-a-stick endoscopes usually do not provide a focus means. However, large diameter flexible endoscopes used in gastroenterology do often have moveable detectors or lenses providing focus.

For smaller chip-on-a-stick endoscopes, all of the optical elements in the objective lens assembly are optimized for the small aperture which allows great depth of field. It is not the case that the aperture could be removed for increased brightness. The advantage is that no motion (focus) is required and when provided with powerful illumination systems in the visible light the overall system can perform well given the constraint of illumination.

A focus means becomes an area of distinction between a chip-on-a-stick endoscope and a wand imaging device, referred to as an intraoral or dental camera, as well. Both chip-on-a-stick endoscope and a wand imaging devices contain the detector plane in the distal or forward portion of the device directly behind the objective lens assembly. The intraoral or dental camera is often required to be used in stand off mode, a distance that is greater than endoscopy requires. The distinction results from the use; endoscopy is done in closed surgical or diagnostic sites, the intraoral devices are used external to the body or inserted in natural cavities such as the mouth. In such stand off modes, not the mouth but full face views, great amounts of illumination would be required to satisfy the large change in s and s' (the optical path length on either side of the objective lens) in the intraoral or dental camera where to be fixed focus. Therefore, intraoral or wand like dental cameras frequently contain a means to move the detector plane, or focus the device. Using a faster F number, with inherently less depth of field but higher sensitivity, and by moving the detector plane a lower powered illumination system is required. This allows a wand with near IR capabilities to accommodate large changes in distances to the object of interest, thereby allowing a faster optical system to be designed, a characteristic that requires variable focus, but provides higher inherent resolution, and more conservative illumination sources.

Endoscopes and wands are generally designed to visualize in the visible spectrum. However, fluorescent dyes, such as indocyanine green (ICG) (Akorn, Inc., Buffalo Grove, Ill.) are commonly being used to image anatomy in the infra red spectrum. Use of ICG is described in, for example, U.S. Pat. No. 6,915,154, which is incorporated herein by reference in its entirety. Once excited, ICG emits in the infra red spectrum at about 825 to about 835 nm. FIG. 1 shows the excitation and emission spectrum of the ICG composition sold by Akorn, Inc. There is therefore a need for endoscope and wand devices that are capable of imaging and visualizing in the infrared spectrum.

MODES FOR CARRYING OUT THE INVENTION AND INDUSTRIAL APPLICABILITY

Figure 1:
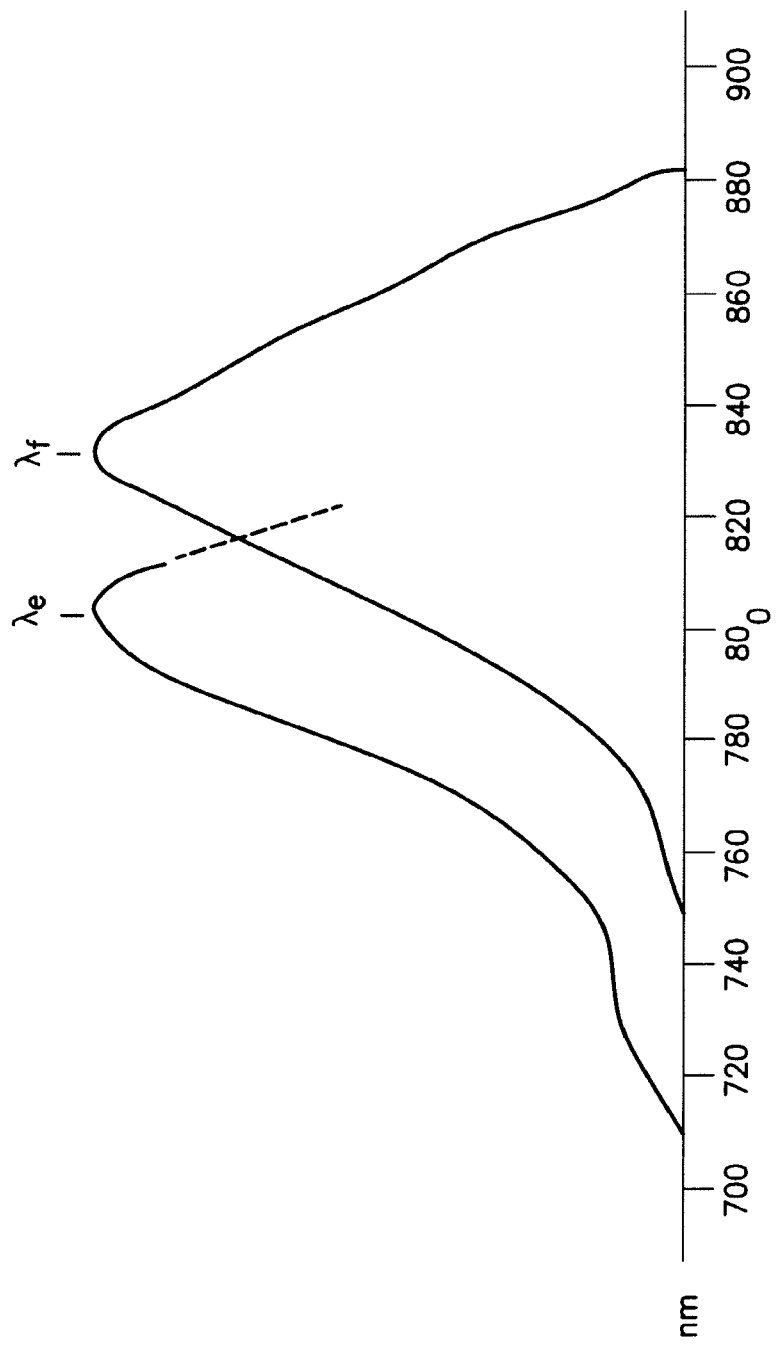
FIG. 1 shows the excitation and emission spectrum of the ICG composition sold by Akorn, Inc.

The invention provides endoscope and wand devices and systems for imaging in the infrared spectrum, and preferably in multiple spectrums at least one of which is infrared. Imaging of fluorescent emissions in the infrared spectrum is particularly difficult because the near infrared light emitted by a fluorescent dye may be an order of magnitude or more lower than the visible light reflected or emitted by a subject. A "device" is any hand-held instrument designed to view or image anatomy, either inside or outside a patient's body.

In certain embodiments, the invention provides an endoscope or wand device having relay optics such as glasses. The transmitting members have a coating that transmits between about 95% and about 99.5% of energy at a wavelength within the infra red spectrum.

In some embodiments, the invention provides a prism assembly for separating visible light from infra red light. The prism assembly contains at least one channel configured to receive and transmit light in the visible spectrum and at least a second channel configured to receive and transmit light in the infra red spectrum.

Hereinafter, aspects in accordance with various embodiments of the invention will be described. As used herein, any term in the singular may be interpreted to be in the plural, and alternatively, any term in the plural may be interpreted to be in the singular.

Definitions

"Approximately", "substantially" and "about" each mean within 10%, preferably within 6%, more preferably within 4% even more preferably within 2%, and most preferably within 0.5% of the stated number or range "Computer" as used herein, refers to a conventional computer as understood by the skilled artisan. For example, a computer generally includes a central processing unit that may be implemented with a conventional microprocessor, a random access memory (RAM) for temporary storage of information, and a read only memory (ROM) for permanent storage of information. A memory controller is provided for controlling RAM. A bus interconnects the components of the computer system. A bus controller is provided for controlling the bus. An interrupt controller is used for receiving and processing various interrupt signals from the system components. Mass storage may be provided by diskette, CD ROM, DVD, USB stick, or hard drive. Data and software may be exchanged with computer system via removable media such as the diskette, USB stick, or CD ROM. A CD ROM or DVD drive is connected to the bus by the controller. The hard disk is part of a fixed disk drive that is connected to the bus by a controller. User input to the computer may be provided by a number of devices. For example, a keyboard and mouse may be connected to the bus by a controller. An audio transducer that might act as both a microphone and a speaker may be connected to the bus by an audio controller. It will be obvious to those reasonably skilled in the art that other input devices, such as a pen and/or tablet may be connected to the bus and an appropriate controller and software, as required. A visual display can be generated by a video controller that controls a video display. Preferably, the computer further includes a network interface that allows the system to be interconnected to a local area network (LAN) or a wide area network (WAN). Operation of the computer is generally controlled and coordinated by operating system software, such as the Solaris operating system, commercially available from Sun Microsystems, the UNIX® operating system, commercially available from The Open Group, Cambridge, Mass., the OS-X® operating system, commercially available from Apple, Inc., Cupertino Calif. or the Windows XP® or VISTA® operating system, commercially available from Microsoft Corp., Redmond, Wash., or the Linux open source operating system available from multiple sources. The operating system controls allocation of system resources and performs tasks such as processing scheduling, memory management, networking, and I/O services, among things. In particular, an operating system resident in system memory and running on the CPU coordinates the operation of the other elements of computer.

"Subject" as used herein, refers to any animal. The animal may be a mammal. Examples of suitable mammals include, but are not limited to, humans, non-human primates, dogs, cats, sheep, cows, pigs, horses, mice, rats, rabbits, and guinea pigs.

As used herein, "wavelength of interest" refers to light in both the visible and infra red spectrum. In some embodiments, it refers to light in only the infra red spectrum. In some embodiments, it includes light at the wavelength at which ICG fluoresces. In some embodiments, it includes light between about 825 and about 835 nm. In some embodiments, it includes light wavelength(s) at which one or more other fluorescent dyes emit energy when excited. The invention is drawn to endoscopes and wands that can advantageously be used for visualizing and imaging in the infrared spectrum, and preferably in both the infrared and visible spectrums.

The term "endoscope", as used herein, will be understood to encompass wands and laparoscopes, as well as endoscopes and other similar devices.

Figure 2:
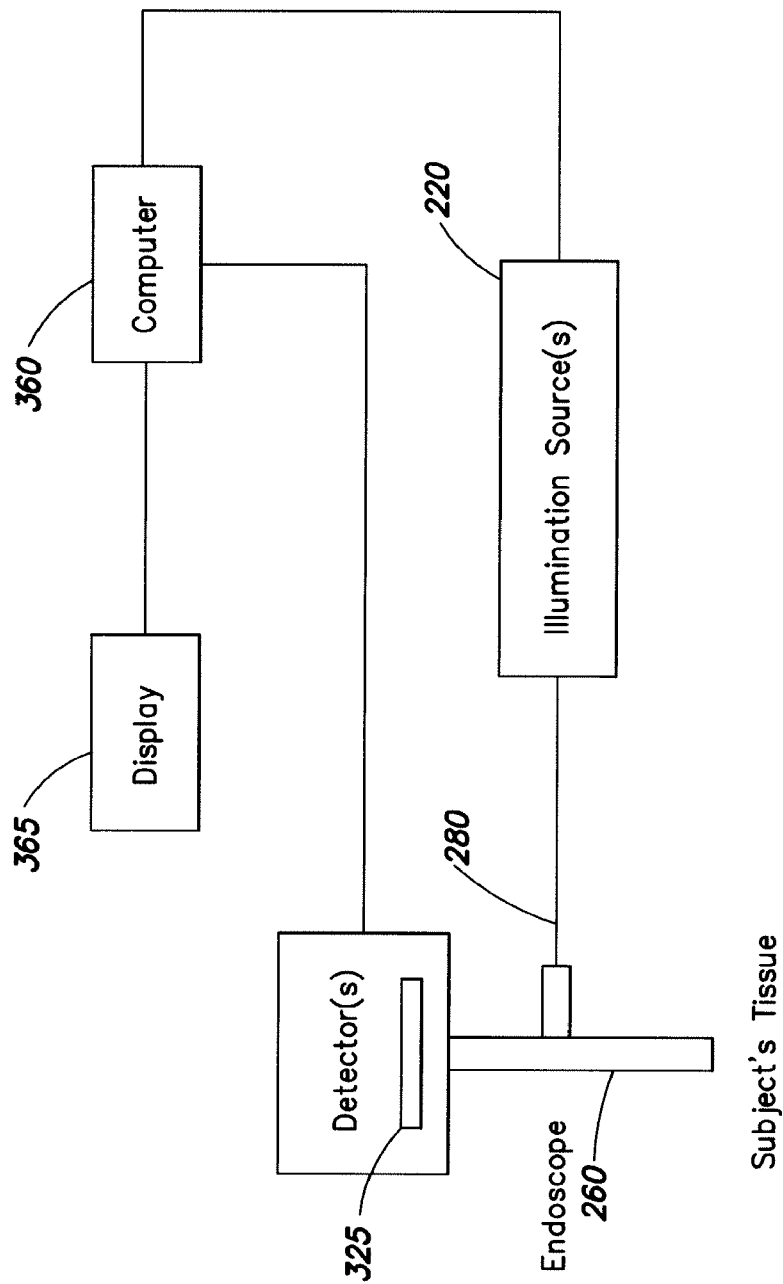
FIG. 2 illustrates an endoscopic system.

FIG. 2 illustrates a highly schematic view of an endoscopic system. The endoscope 260 is placed in the proximity of a subject's tissue or inside a natural or surgically created opening in the subject.

An endoscope may have one or more illumination sources 220. Preferably, the illumination 220 source emits radiation having wavelengths in the infrared spectrum, and images in the infrared spectrum. Infrared radiation at certain wavelengths can excite a fluorescent dye that has been administered to the patient and cause the fluorescent dye to emit radiation. In certain embodiments, imaging may be performed in multiple discrete bands of the spectrum. For example, imaging may occur in two distinct infrared bands, in the infrared and visible spectrum, or in the infrared and ultraviolet spectrum. In preferred embodiments, both visible and infrared light is emitted by one or more illumination sources 220 for imaging in both the visible or infrared spectrums.

The one or more illumination sources 220 is in electrical communication with the computer 360. Through a computer interface, a user causes an illumination source(s) 220, such as an HPLD, to fire or otherwise emit radiation.

The illumination source 220 can be coupled to the existing fiber optics in the endoscope or wand or coupled to an external cannula embedded with fiber optics or containing a working channel with sufficient diameter to place a fiber optic or fiber optic probe for the transmission of an excitation wavelength. The endoscope itself may contain a working channel sufficiently large for a laser fiber to be inserted and in that case a supplementary cannula or sheath for an excitation source would not be required. Other suitable illumination sources are described below.

In some embodiments, the illumination source 220 is in optical communication with endoscope 260 by cable(s)/cannula(s) 280. If the illumination source 220 is a single emitter laser then it could be coupled to one cable 280. Alternately, a bar laser would require multiple fibers, which might be packed in the same or in multiple cables. Cable(s) 280 may connect to fibers integrated into the tubular portion of the endoscope 260 or to a sheath surrounding part or all of the endoscope 260. Fibers in the tubular portion or sheath then relay the illumination to the patient's tissue.

Light from the illumination source(s) 220 is transmitted to the subject's tissue. Reflected or emitted light from the subject's tissue is then transmitted to one or more detectors. These detector(s) are in electrical communication with computer 360, which receives the images collected by the detector(s) and causes them to be displayed on a display 365. The computer 360 may further include software for image processing.

I. Illumination Sources 220

The first step in imaging a dye (that is administered to a patient) that emits in the infrared spectrum is to excite the dye. The dye may be excited in the visible, ultraviolet or infrared spectrum. Preferably, the dye is a fluorescent dye. More preferably, the dye is a tricarbocyanine dye. Most preferably, the dye is ICG. In some embodiments, multiple dyes may be used for imaging.

In one embodiment, the light source only emits light in the infrared spectrum. In some embodiments, light in both the visible and infrared spectrum is emitted. In some embodiments, the device of the invention, such as an endoscope or wand includes one or more LEDs that emits light in the infrared spectrum and groups of 3 LEDs, producing red, green, or blue illumination, respectively, for visible imaging. In certain embodiments, the device includes LEDs producing or restricted to infrared illumination combined with one or more white light LEDs. Light sources may be bulbs or arc sources of metal halides, halogens and xenon that emit in the blue, green and red and infra red wavelengths. LEDs and other light sources that emit in both the visible and infrared spectrums are well known to the skilled artisan.

High power laser diodes (HPLDs) may also be used within the scope of the invention. Examples of HPLDs include AlInGaAsP lasers and GaAs lasers which are well known in the art. Such sources can be single diodes (single emitters), or diode-laser bars, which are made from edge emitting semiconductor chips. Such sources can be operated in continuous mode (CW), quasi-CW, or pulsed mode.

These sources are capable of being remotely mounted in the system and can be brought to the optical system used for viewing fluorescence via fiber coupling. This removes the HPLD, a powerful electrical device, from intimate contact with the patient, physician or technician.

The excitation wavelength, $\lambda_e$, of ICG is 805 nm in whole blood. The range of excitation wavelengths capable of exciting ICG ranges from approximately 710 nanometers to 840 nanometers, or more. This range overlaps the fluorescence range of ICG whose peak, $\lambda_f$, is 835 nanometers. It is therefore necessary to use a narrow source such as an HPLD or similarly filtered Metal halide, Xenon, or Tungsten halogen sources of radiation by means of an excitation or primary filter or filters to excite the ICG.

HPLDs, made of AlInGaAsP/GaAs, have as their peak nominal output a wavelength of 808 nm, with a tolerance of +/−3 nanometers. A driving circuit is necessary to provide power to the HPLD, the current and voltage of which can be varied to lower the peak wavelength to 805 nm, the peak absorption of ICG.

Within the endoscope proper, an illumination pathway may take one of two forms or a combination of the following: an integrated annulus of fiber optic fibers encircling the optical elements for the transmission of visible light, and or an annulus of fiber optic fibers transmitting the energy from an IR excitation source contained within a sheath or cannula into which the imaging device is inserted.

II. Endoscopes and Wands

Figure 3:
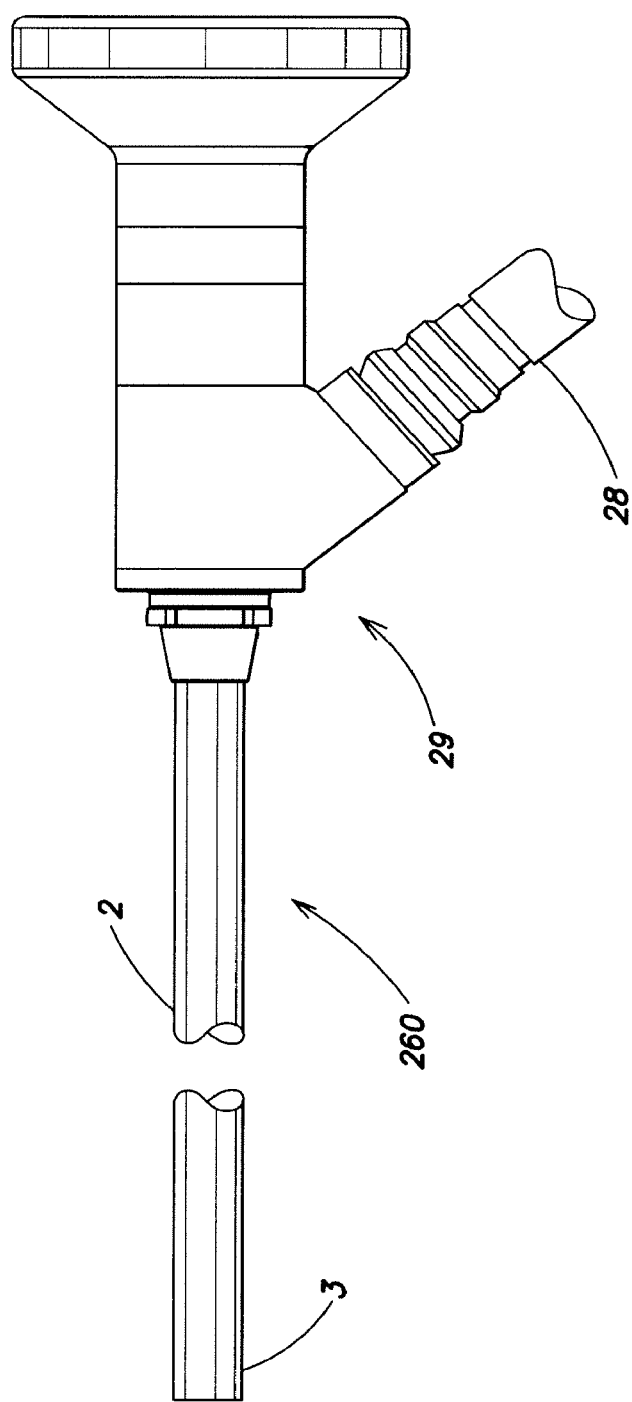
FIG. 3 illustrates an endoscope.
Figure 4:
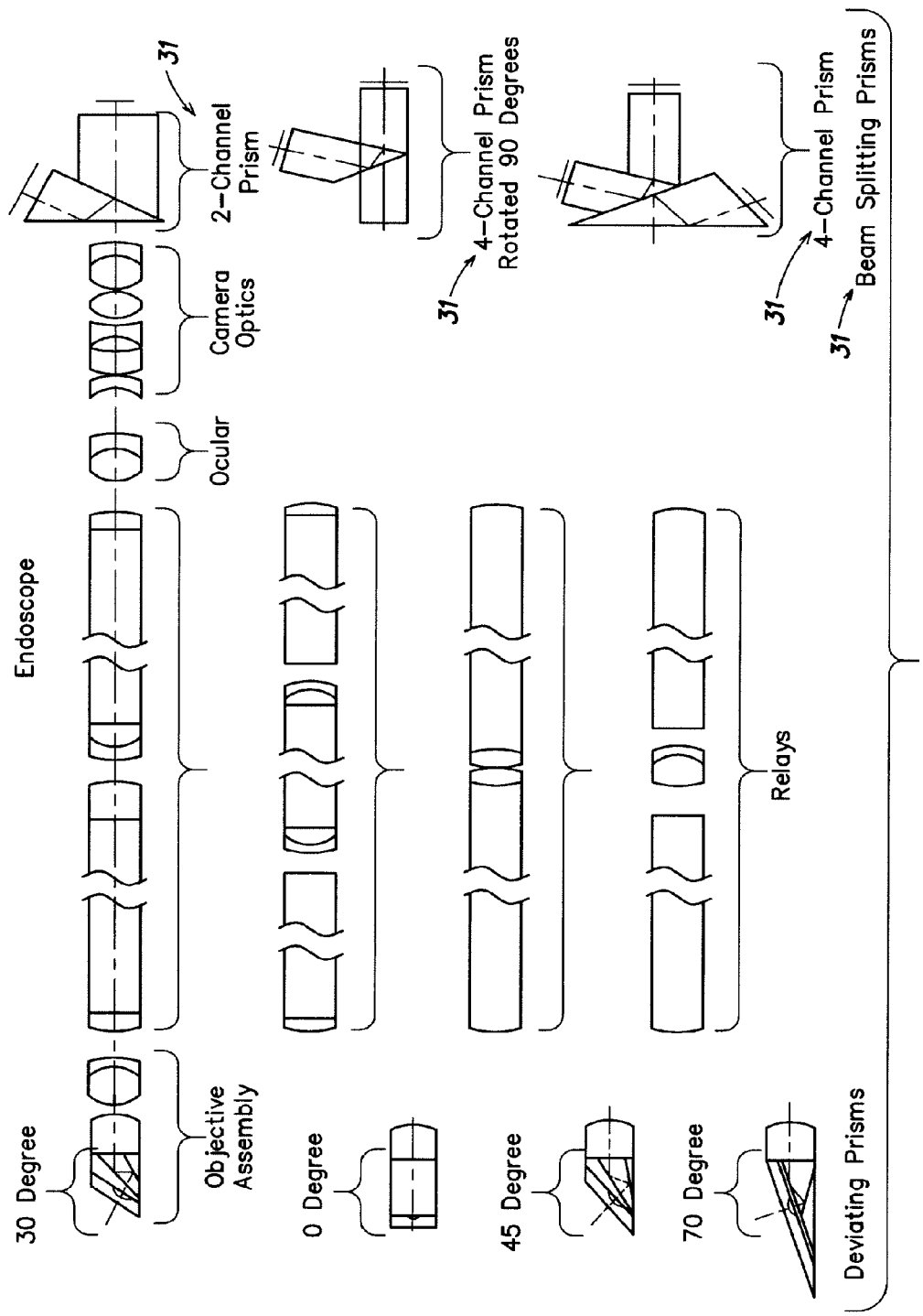
FIG. 4 illustrates certain endoscope components. The left side of FIG. 4 illustrates multiple examples of objective assemblies, only one of which would commonly be used in any particular endoscope. The middle of FIG. 4 illustrates multiple examples of relays, of which only one would commonly be used in a particular endoscope. The right hand side of FIG. 4 illustrates a 2 channel prism or a 4 channel prism (the bottom two drawings showing the same 4 channel prism from different views). Commonly only one of a 2 or a 4 channel prism would be used in any particular endoscope.

For example, endoscope 260 is shown in FIG. 3, and certain components are shown in FIG. 4. The endoscope 260 may include a distal section 3, a relay section 2, and a proximal section 29. Light travels from an illumination source 220 (not shown) to fiber cable 28 through the relay section 2 and to the distal section 3. Reflected or emitted light travels from the distal section 3 having the objective assembly, through the relay section 2 and then through the proximal section 29 having prisms to the detector(s) 33 (shown in FIGS. 9 and 10) in proximal section 29. The detector(s) 33 detect the light and can form an image. The endoscope 260 may include an ocular and camera optics in the proximal section 29 to magnify or focus the image.

All the optical elements along the 3 segments of the longitudinal axis of the endoscope and wand are required to be coated for low reflectivity for (preferably all) transmitting elements across all the wavelengths of interest, high reflectivity in all wavelengths of interest for reflecting surfaces contained within the distal section, and high separation ratios in the proximal beam-splitting section. An embodiment for a wand configuration contains in its distal portion both a deviating and a beam-splitting prism assembly. Preferably each optical coating on a transmitting optical element is optimized for an angle of incidence of light that is orthogonal or substantially orthogonal to each surface along a vector describing the opto-mechanical axis of the system within a range of plus or minus 10, 9, 8, 7, 6, 5, 4, 3, 2, or 1 degrees. This does not apply to the objective lens assembly where the departure from normal to the surface is greater.

The wand has the same components as shown in FIGS. 3 and 4, but generally has a different form factor since it is optimized for use outside a person's body while an endoscope is optimized for insertion into a person's body.

A. Distal Section 3

The distal section 3 of the inventive device may include an optical assembly taking the form of an inverse telephoto with a distal negative power lens group, a prism assembly 18 to deviate the line of sight within this deviating assembly and a positive lens group. A deviating prism assembly 18 is contained between the distal lens group characterized by its negative optical power and a proximal lens group characterized by its positive power. This optical form (− +) is commonly called an inverse telephoto. Distal sections of endoscopes and other devices are well known in the art, and are described in, for example, U.S. Pat. No. 4,655,557 that is incorporated herein by reference in its entirety.

Figure 5:
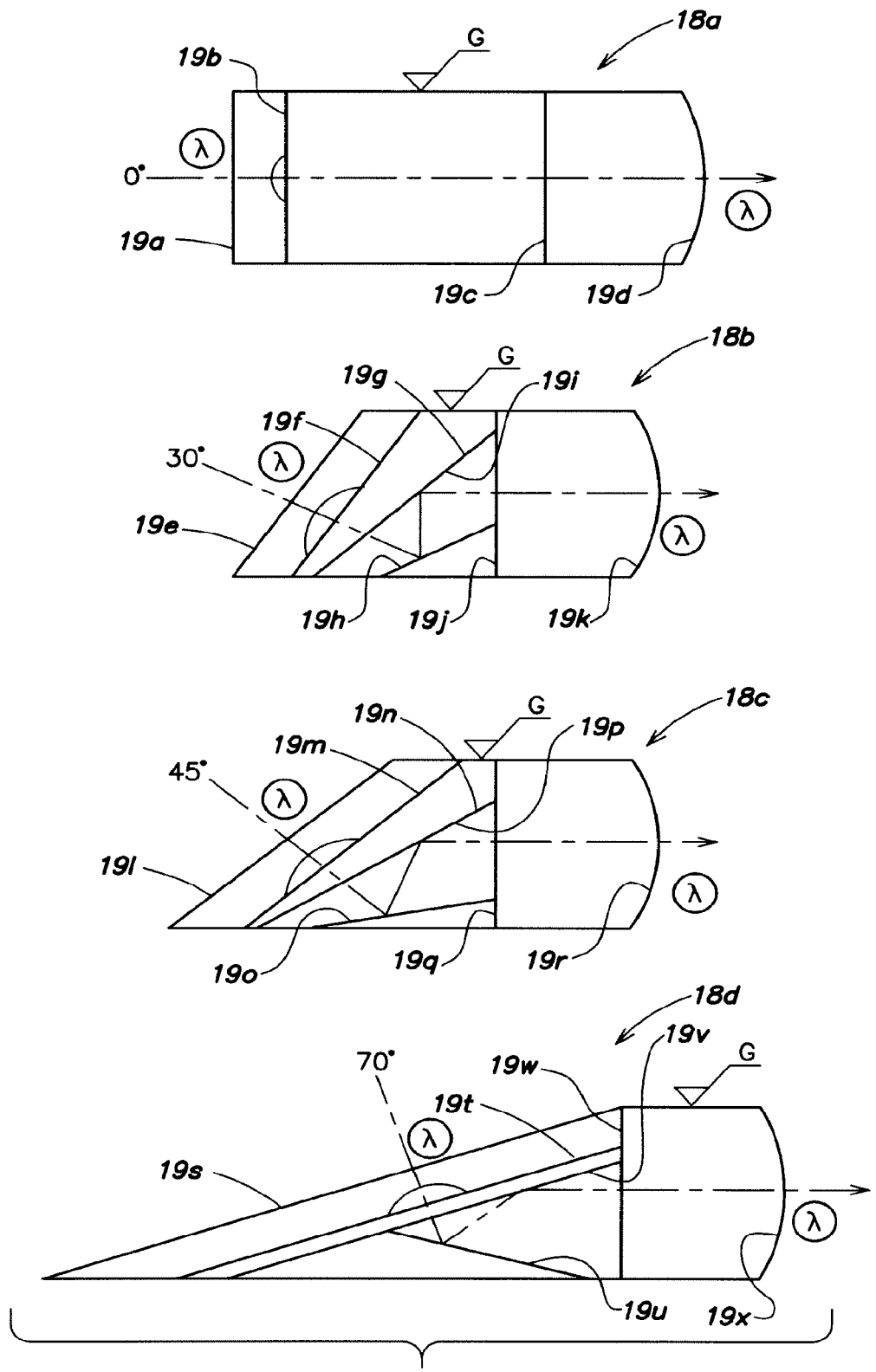
FIG. 5 illustrates deviating prisms.

Deviating prism assemblies 18 are routinely placed within the space between the two powers of endoscopes used in visible wavelengths, as described, for example, in U.S. Pat. No. 4,917,457, which is incorporated herein by reference in its entirety. Such deviating prisms allow the endoscope to be rotated around the shaft axis for a larger effective field of view. Examples of deviating prisms 18 are shown in FIG. 5. The angles shown are exemplary since a skilled artisan may design deviating prisms to facilitate the passage of the full beam diameter or substantially the full beam diameter of the objective lens assembly through the prism with the following constraints, first that the ray path axis exiting the negative group of the objective lens be coincident or approximately coincident with the optical axis of the prism assembly group, second that the ray path enter the front face of the prism assembly perpendicular or approximately perpendicular to the face of the first surface of the prism assembly, thirdly, that the ray path exit the last surface of the deviating prism assembly perpendicular or approximately perpendicular or normal to the face of the last prism component, and fourthly that the exit ray path optical axis be coincident or approximately coincident with the optical axis of the following optical components.

The deviating prisms of the invention must displace or deviate the line of sight. For example, the first prism (FIG. 5(a)) has a zero percent deviation, meaning that the wavelengths of interest are transmitted through each of the surfaces 19a, 19b, 19c and 19d.

In FIG. 5(b), the line of sight is deviated thirty degrees. This means that the line of sight and coincident beam path is transmitted through surface 19e, 19f, 19g, reflected by surface 19h and 19i, and then transmitted through surfaces 19j and 19k.

FIG. 5(c) shows an example of a 45° deviating prisms. The line of sight and coincident beam path is transmitted through surfaces 19l, 19m and 19n, reflected by surfaces 19o and 19p, and then transmitted by surfaces 19q and 19r.

A final example, FIG. 5d, shows an exemplary 70° deviating prism. The line of sight and coincident beam path is transmitted through surfaces 19s and 19t, reflected by surfaces 19u and 19v, and then transmitted through surfaces 19w and 19x.

Thus, the reflective surfaces (e.g., 19h, 19i, 19o, 19p, 19u and 19v) must be coated with a substance that reflects light in the infrared in preference to one that is optimized for the reflection of visible only. In preferred embodiments, in which the wavelengths of interest are in the emission range of ICG, the reflective surfaces are coated so that they reflect light between about 800 and about 850 nm, preferably between about 825 nm and about 835 nm. Most preferably, the reflecting surfaces reflect both infrared and visible light. This high reflectance of wavelengths in the infra red spectrum, and preferably in both the visible and infra red spectrums, is achieved with a coating of gold, silver or aluminum. Gold is particularly preferred for reflecting only wavelengths in the near infra red spectrum. Silver is particularly preferred for reflecting wavelengths in the visible and near infra red spectrums. These coatings can be applied directly to the reflecting prism surface and are between about 1 and about 20 micrometers in thickness, and preferably between about 1 and about 10 micrometers in thickness. They can be purchased from, for example, TYDEX J.S. Co.

(St. Petersburg, Russia) and vapor deposited onto the surface of interest by any number of thin film coaters in the world using vacuum deposition chambers. Gold coatings are especially preferred because they are known to reflect well in the near IR and withstand autoclaving processes. In some embodiments, any coating that reflects at least 80%, preferably at least 90% and most preferably at least 95% of light energy that is within the wavelengths of interest may be used. A second coating, such silicon dioxide ($SiO_2$), magnesium fluoride, silicon monoxide or a dielectric overcoat may be applied. Such coatings can be purchased from, for example, OFR, Inc., Caldwell, N.J.

The transmitting prism surfaces (e.g., 19a, 19b, 19c, 19d, 19e, 19f, 19j, 19k, 29l, 19m, 19q, 19r, 19s, 19t, 19w and 19x each transmit wavelengths of light in the infrared and the visible spectrums. Any surface that is glued and not air-glass does not need an anti-reflecting coating applied.

B. Transmitting Members

The vast majority of optical surfaces that are used for transmitting the wavelengths of interest ("transmitting members") are in the relay section. The discussion of transmission coatings, below, is framed in reference to transmitting members in the relay section, though it is equally applicable to transmitting members in other parts of the endoscope or wand.

The positive lens group in the objective lens assembly forms a real image from the energy received from outside the device for relay to the relay section 2. The relay section 2 includes multiple relay optics (not shown) that relay the image by producing a series of intermediate images to the proximal section 29. The proximal section 29 will be further described below.

Figure 6:
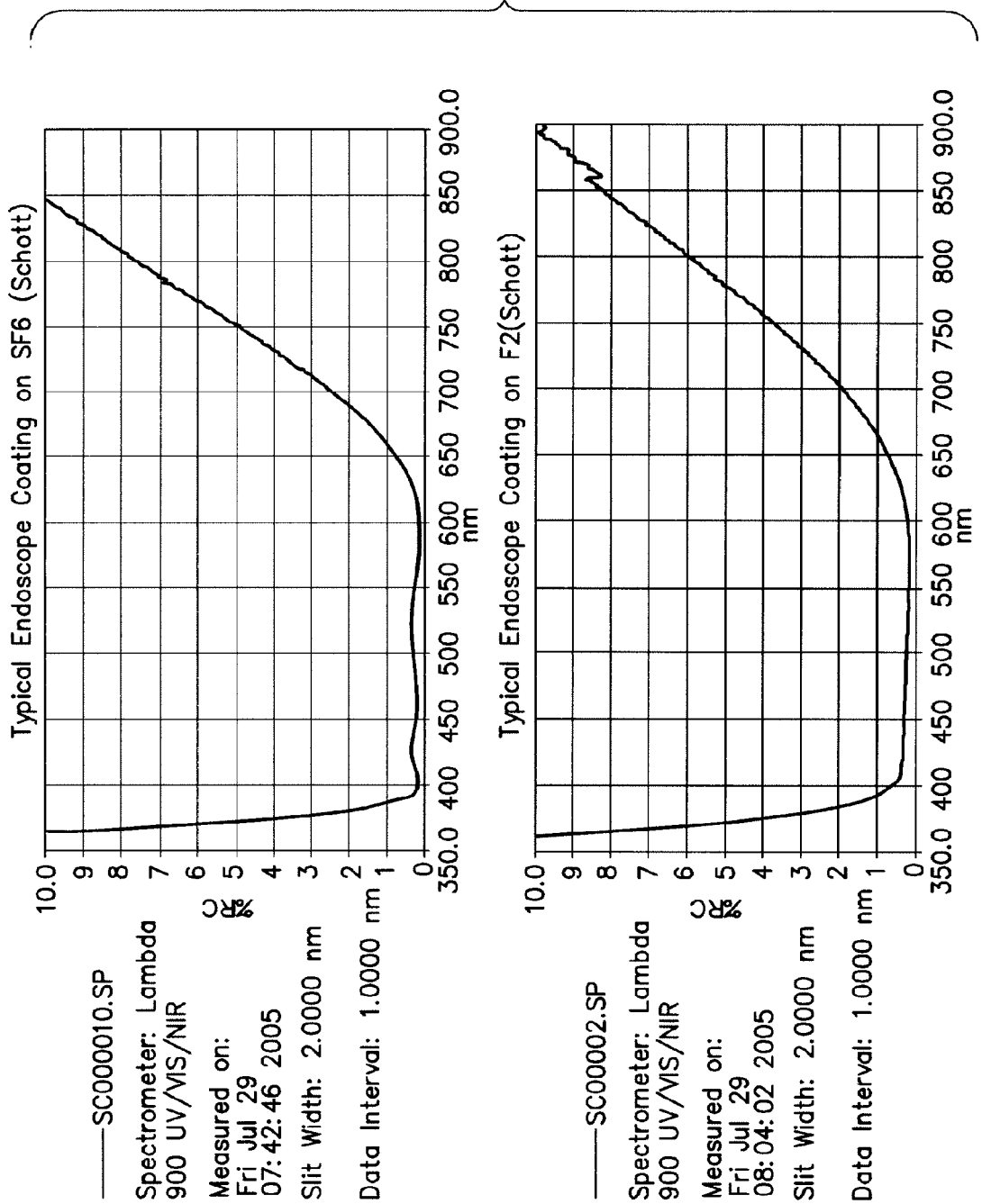
FIG. 6 illustrates representative scans of prior art coatings.

The prior art optical coatings on devices such as endoscopes and wands having relay optics are optimized for the visible spectrum and are biased towards the blue as shown in the representative scans of such coatings on optical glasses, such as F2 and SF6 in FIG. 6. However, such prior art coatings reflect more than 5% of the infrared energy at each glass/air surface. Since a typical relay section 2 could have a large number (e.g., 30-40) glass/air surfaces, the resulting reflectance makes the devices unusable for infrared imaging.

Devices of the invention must have coatings in the relay and other sections that transmit wavelengths in the infrared spectrum that are of interest. Preferably, the coatings have a reflectance of the wavelengths of interest that are no more than about 0.5%, no more than about 0.4%, no more than about 0.3%, no more than about 0.2% and most preferably no more than about 0.5%. In some embodiments, coated relay optics each reflect between about 0.5% and about 5% of the wavelengths of interest, and preferably between about 0.5% and about 3%.

The wavelengths of interest will depend on the application. For example, if ICG is injected into and excited in a human being, the wavelengths of interest will include the wavelengths at which ICG emits energy. In such an application, the wavelengths of interest might be 825-830 nm. In a preferred embodiment, the coating is optimized to minimize reflectance both in the infrared and visible spectrums, thus allowing viewing in both the infrared and visible spectrums. The visible spectrum is commonly considered to be between about 400 nm and about 700 nm.

The coating preferably includes alternating layers or pairs of layers. These pairs include a high and a low index coating material that together make up a pair. Suitable pairs include $TiO_2$ and $MgF_2$, $TiO_2$ and $SiO_2$, Zirconium Oxide ($ZrO_2$) and $MgF_2$, and tantulum pentoxide ($Ta_2O_5$) and $SiO_2$. The number of repeating pairs that may be used is between about 2 and about 100, preferably between about 2 and about 50, between about 2 and about 40, between about 2 and about 30, and between about 2 and about 20 for any optical surface. In some embodiments, the coating has a minimum of 6, 7, or 8 pairs. In certain embodiments, the coating has a minimum of 4 pairs. In some embodiments, the coating has a minimum of 10 pairs. A coating may have one or more different pairs. A useful low index material is $SiO_2$ with an index of refraction of approximately 1.45 in the visible. $SiO_2$ would be paired with a high index material such as $Ta_2O_5$, which has an index of 2.4 in the visible, in slightly different ratio when placed on a low index of refraction glass, such as BK7, than on a high index glass, such as N-SF57. In some embodiments, a high refractive index material is one having an index of refraction from about 1.9 to about 2.4 in the visible spectrum as measured at 633 nm. A low refractive index, in some embodiments, is one having an index of refraction from about 1.45 to about 1.8 as measured at 633 nm.

Figure 7:
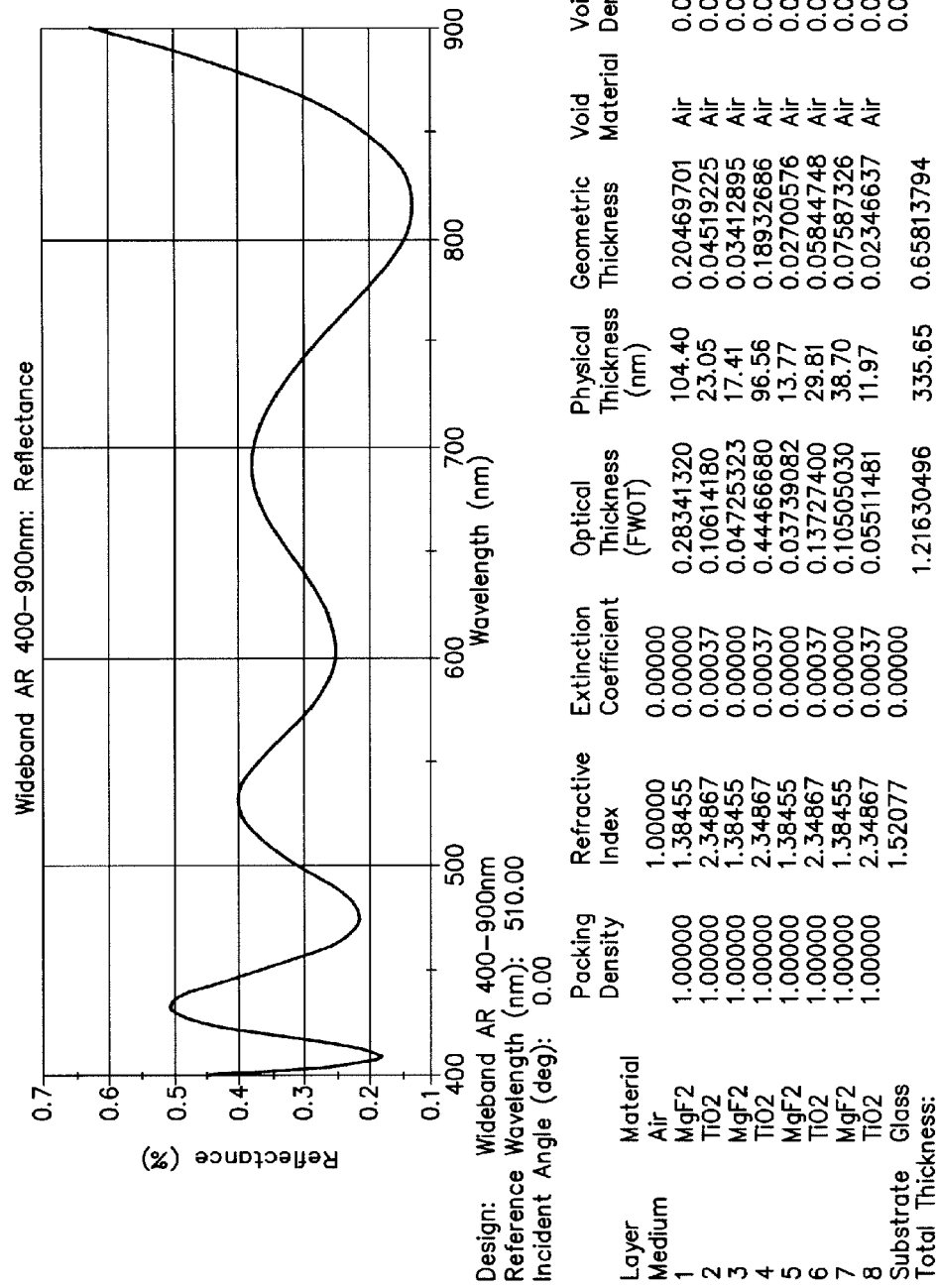
FIGS. 7 and 8 each illustrate details of coatings.

FIG. 7 illustrates an example of one such coating that is optimized to have low reflectance around the emission range of ICG. It is comprised of alternating layers of $MgF_2$ and $TiO_2$.

Figure 8:
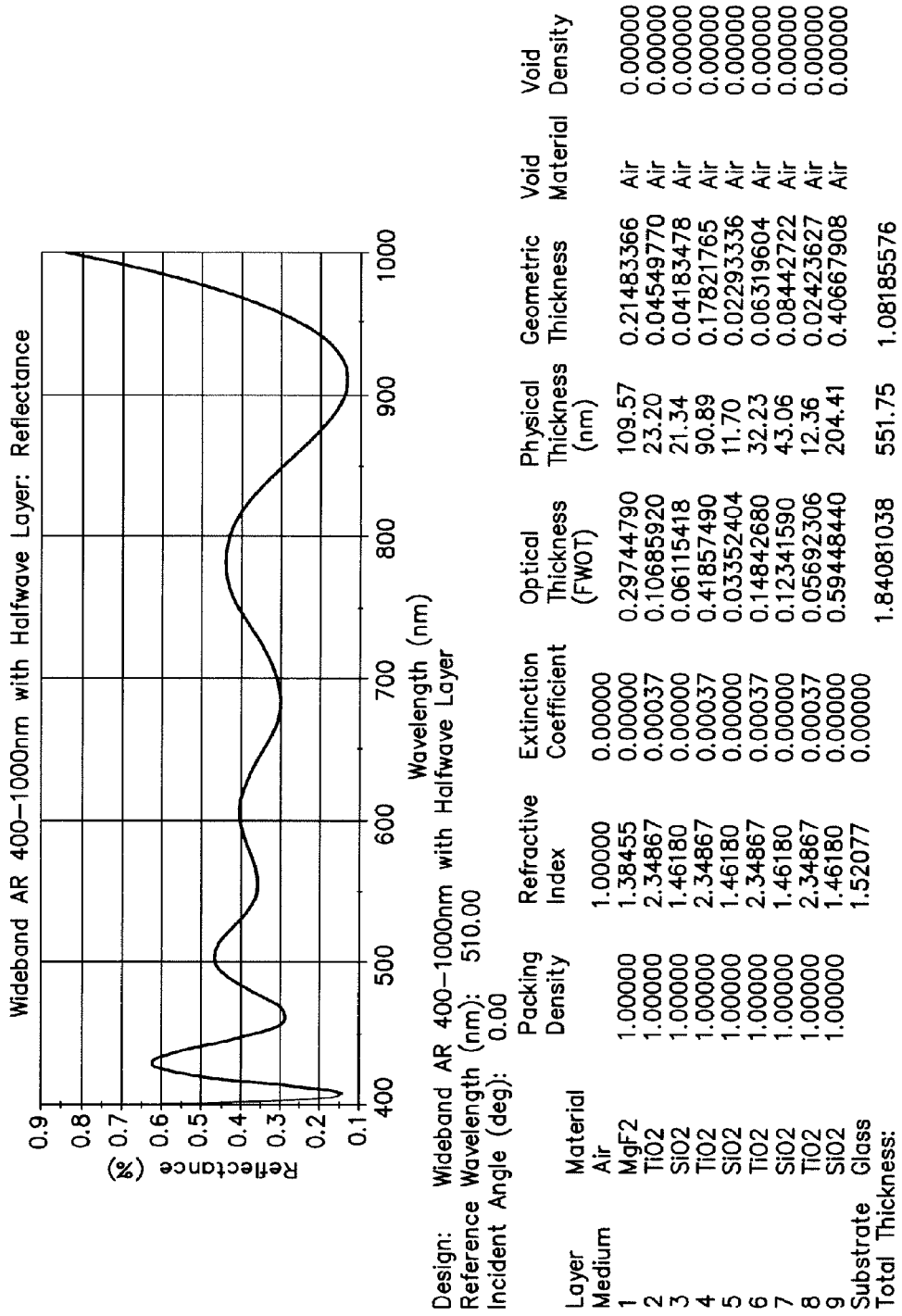

FIG. 8 illustrates another example of a low reflectance coating suitable for use in the relay optics of the invention. This coating has alternating layers of $SiO_2$ and $TiO_2$, and one pair of $MgF_2$ and $TiO_2$.

In choosing glasses or optical surfaces, the skilled artisan considers a number of factors to favorably correct the optical aberrations and cover the desired field of view on the detector chosen with a minimum of uncorrected residual aberrations. In choosing the glass type, factors to consider are measure of bending power, index, a measure for their dispersing power, and geometric variables such as radius of curvature, thickness of glass and thickness of air, the order of glasses through the system and other factors well within the ability of the skilled artisan. Glasses used in the relay sections of the devices of the invention could, for example, cover a range of about 1.5 to about 2.0 as a measured by their index of refraction. While there are many air-glass surfaces in a device of the invention, not every one will represent a distinct coating choice. There may be groupings of glasses with similar indices that will be coated in the same vacuum deposition chamber run. For example, a grouping might be made of glasses with an index range of 1.5 to 1.65, 1.65 to 1.7, and so forth. The judgment will be made based on performance of the whole stack of pairs used for the particular coating design. The criteria for the design goals will include wavelengths and or range of interest chosen and their relative weighing at measurable points, angles of incidence chosen and their relative weighing, environmental considerations, and cost.

The thin film designer, in designing a coating suitable for one or more relay glasses, considers, for example, pairs of high and low index material, their individual thickness (in optical terms, i.e. they are wavelength dependent because they have an index of refraction), their pair thickness, and the substrate glass index. Antireflective coatings and dielectric mirrors are discussed in the publication Electromagnetic Waves and Antennas, published by Sophocles J. Orfanidis on the website <http://www.ece.rutgers.edu/~orfanidi/ewa> which are attached at the end of this specification.

In some embodiments, devices such as a "chip-on-a-stick" do not use relay optics, but rather pass light energy from the distal section 3 to the proximal section 29 through fiber optics. In such embodiments, the skilled artisan will understand that there are no relay optics to be coated. Chip-on-a-stick designs eliminate the proximal position of the detector and move said detector plane to the image plane of the objective lens assembly. The preferred inventive chip-on-a-stick design only images in the infra red spectrum though those that image in both the infra red and visible spectrum are within the scope of the invention.

C. Summary of Dichroic Filter and Cameras

Referring to FIGS. 3, 4, 5, 9, 10, and 11, the beam splitting proximal prisms/dichroic filters 31 receive light from relay section 2 or the exit pupil of a distal section 3 and focuses light onto the detectors 33. In some embodiments, the relayed image only includes light in the infra red spectrum. This image is directed to detector 33b which may be a single charge coupled device (CCD) or complementary metal-oxide semiconductor (CMOS) or any other type of detector that can detect infrared light. While infrared blocking filters are commonly used to block out infrared light in endoscopes that do not obtain infrared images, the skilled artisan will understand that such filters should not be used in this embodiment.

In certain embodiments, the device is configured to visualize both in the infrared and visible spectrum. Thus, the light energy received from the distal and relay sections is in both the visible and infrared spectrum. In this embodiment, the proximal prisms 31 separate the wavelengths and relay them to detectors capable of detecting appropriate wavelengths.

The proximal prisms 31 must have substantially equal path lengths to each detector 33 to yield similar magnifications for such comparisons or superimposed imaging. These proximal prisms 31 could take many forms, but they share approximately equal path lengths per detector and the use of dichroic filters that substantially enhance the optical efficiency or throughput of the system when compared with metalized beam splitter coatings.

Preferably, the ratio of the unfolded optical path length to diameter ratio in each light pathway through the proximal prism assembly is given by:

$$1.75W \leq L \leq 3W$$

where

W is the diagonal of the exit face of the unfolded path of any or all of the prisms L is the path length along the optical axis and corresponds to the focal length of the focusing optics minus an air space on either side of L As described above, ICG has a peak excitation wavelength at 805 nm. The range of excitation wavelengths capable of exciting ICG ranges from approximately 710 nanometers to 840 nanometers, or more. This range overlaps the fluorescence range of ICG whose peak, $\lambda_{fl}$ is 835 nanometers. The challenge is that the fluorescent return signal, in the near infrared (NIR) for example, can be significantly lower than that of the visible channels which are transmitting a scattered return. This differential between low fluorescent return and normal visible return requires not only highly efficient coatings not found on normal endoscopes and wands but also improvements associated with the detector assembly. An optical design optimized for the visible is slightly different than that of an optical design for visible (VIS) plus NIR imaging. However, a comparable design can be used for both regions, if the back focus is allowed to vary in length along the z or optical axis. A NIR image is formed behind that of a visible wavelength of either Red, Green or Blue because NIR wavelengths are longer; hence we want to vary the back focus of the NIR image found exiting the face of the proximal prism assembly.

In certain embodiments, the proximal prism assembly 31 is organized by wavelength in a short to long or long to short order by means of dichroic beam-splitting coatings contained within the prism assembly. For example, in the case of a 4 channel prisms associated with three detectors that detect in the visible range, and one detector that detects in the infrared range, $\lambda 1 < \lambda 2 < \lambda 3 < \lambda 4$. Thus, $\lambda 1$, $\lambda 2$, and $\lambda 3$ are associated with 400 nm to 700 nm and $\lambda 4$ is dedicated to 810 nm to 870 nm, approximately for the long pass configuration.

An imaging pathway will require a barrier or secondary filter required to block the excitation radiation from reaching the detectors. This barrier filter is a dichroic filter made up of high and low index materials evaporated onto a substrate whose arrangement disposes the filter to have a lower and upper cutoff encompassing a range of wavelengths above that of the excitation wavelength, $\lambda_e$, whose peak is 805 nm for ICG. The skilled artisan will understand that other dyes will have other $\lambda_e$ and will hence require different filters for imaging. Wavelength ranges below the cutoff frequency must be blocked to an optical density of 5 or more so that the detector does not view any portion of the energy from the illumination source, as it may be 2 or more orders of magnitude more intense than the fluorescent response. The dichroic filter may be positioned as a plane parallel plate orthogonal to the optical axis or at some preferential angle to minimize ghost images.

To maximize the lens coupling efficiency to the detector it is important to design the focusing optics and beamsplitting prism assembly to produce a marginal ray angle in the corner of the field which departs from the opto-mechanical axis by 10 or 15 degrees or less from the last optical element in the focusing optics to the detector. It is in this path that the prism assembly 31 is placed. By possessing a shallow marginal ray angle, the ray paths from the various fields within the prism reflect or pass the dichroic filters 31 at a nearly common angle or over a small range of angles. The more similar these angles, the better optical efficiency or throughput for each wavelength range, as dichroic filters by their nature are angle sensitive. Preferably, these angles do not differ from each other by more than 10, 9, 8, 7, 6, 5, 4, 3, 2, or 1 degrees.

Moreover, due to the low signal strength in the NIR path of the weak fluorescent scenes the f-number of the combined NIR VIS focusing and beamsplitting assembly should be as fast as possible for increased sensitivity. The increased sensitivity yields a larger cone angle from the last focusing element through the beamsplitting assembly creating a larger angle range than would be required for VIS imaging alone. Likewise, it is important to make each channel's ray path similar in length so that the resulting image height, magnification, on all detectors is comparable.

In the case of exceptionally weak NIR fluorescent signals, a cooled or intensified detector may be used on the NIR path. The improved sensitivity may be provided by an intensified CCD (ICCD) or electron multiplying CCD (EMCCD). Similarly, an intensifier or cooler means may be integrated to the infrared detector or beamsplitting assembly associated with the detector to make an integrated and compact system. A barrier filter may be used adjacent to an infrared detector to remove wavelengths outside those of interest.

Figure 9:
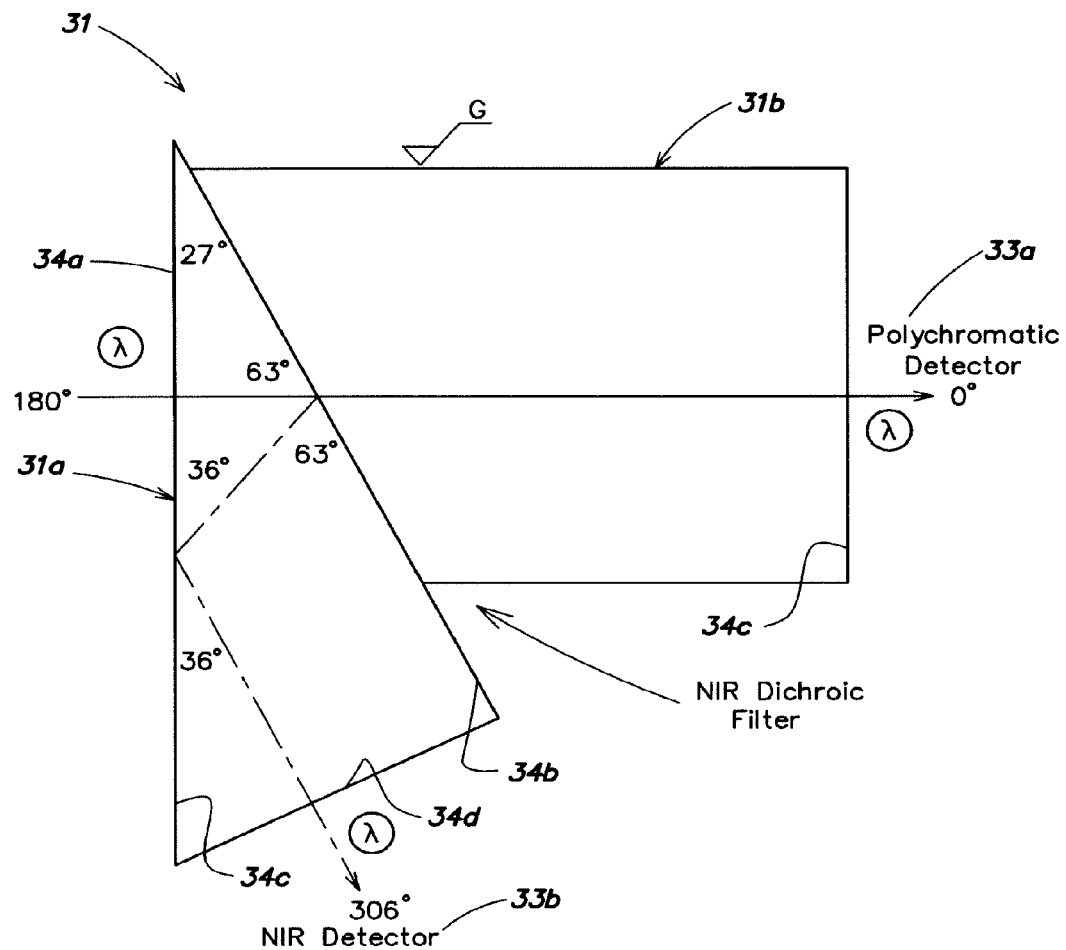
FIG. 9 illustrates a 2 chip prism assembly. Angles shown are merely exemplary.
Figure 10:
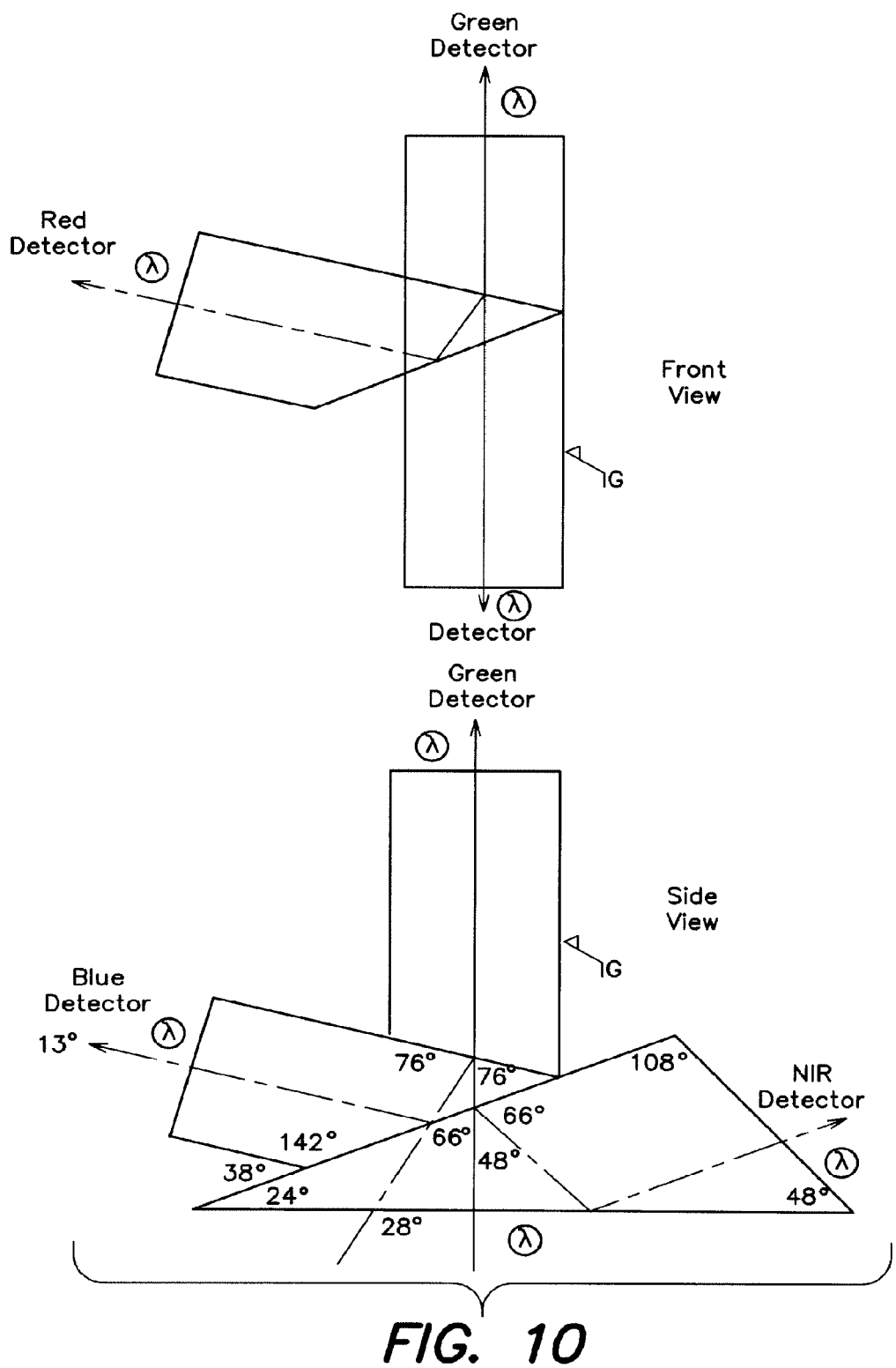
FIG. 10 illustrates a 4 chip prism assembly. Angles shown are merely exemplary.

In certain embodiments, a total of two detectors 33 are used (see e.g., the top prism 31 in FIG. 4 and FIG. 9). One detector 33a detects light in the visible spectrum and the second detector 33*b* detects light in the infrared spectrum. Proximal prism assembly 31 includes a first channel 31*a* and a second channel 31*b*.

Light from the relay section 2 enters channel 31*a* through surface 34*a*. Visible light is transmitted through surface 34*b* and 34*c* to a polychromatic detector 33*a*. The polychromatic detector 33*a* may be a single CCD or CMOS detector with an integrated color filter, such as a Bayer pattern directly on the detector.

Infrared light from relay section 2 is reflected by surface 34*b* and 34*c* onto surface 34*d*, through which it is transmitted to infrared detector 33*b*. Acceptable infrared detectors for any embodiments described herein include silicon. Silicon is the base material of almost all detectors commonly used, and it has a peak efficiency in the near infra red spectrum.

In certain embodiments (FIGS. 4 and 10), a 4 channel prism assembly 31 is used. Prism assembly 31 includes a channel for each of red, green, blue, and infrared, and is coupled to a detector capable of detecting such light. In the case of the 4 channel prism the $4^{th}$ detector is into the page and not seen.

Thus, in certain embodiments, multiple detectors are present in an endoscope of the invention. Preferably, the diagonal of the infrared detector or intensifier associated with the infrared detector is approximately the same length as the diagonal of one or more of the other detectors that image in another spectrum.

Acceptable dichroic coatings which may be used within the context of the 2 and 4 channel prisms (31) may be purchased from Feldmann Optics in Wetzlar Germany, for example. Prism surfaces designed to transmit the wavelengths of interest are preferably coated as described in the transmitting members section, above.

The detectors 33*a* and 33*b* are synchronized and the frame grabber sends signals from all detectors to a computer. The sent data is input in video RAM. The user can access one or both of the visible and/or infrared images. Preferably, the computer includes computer program code that, when executed, gives the user the choice to either see (a) the visible image, (b) the infra red image, (c) both simultaneously (i.e., one superimposed over the other) with controls to dim the visible image, for example, so there is some color information in the displayed image, (d) alternating display of visible and infra red images, and/or (e) side by side viewing in different windows. Preferably, when both infra red and visible images are obtained, the two sets of images are viewed with perfect or substantially perfect registration.

In certain embodiments, field sequential illumination technology, such as described in U.S. Pat. No. 6,960,165, U.S. Pat. No. 6,388,702, and U.S. Pat. No. 6,907,527 may be used. These patents are incorporated herein by reference in their entirety.

A number of functionalities are made possible because detectors 33 detect one or both of infrared and visible light. For example, in embodiments where multiple detectors 33 are used (e.g., an infrared and a visible light detector), the detectors may have an automatic gain function. For example, the two detectors may send information to the computer 360 indicating the amount of energy detected by each. The computer 360 may have computer code for adjusting the gain of each camera based on this information. In some embodiments, the user may adjust the gain of the detectors through a computer interface.

CMOS sensors allow gain manipulation of individual photodiodes, region-of-interest read-out, high speed sampling, electronic shuttering and exposure control. They have a large dynamic range as well as a format for the computer interface. The skilled artisan will understand that the gain of individual pixels may be asynchronously modified in CMOS detectors. For example, areas for which greater performance is required may be made more sensitive. Similarly, in certain areas, response from the detectors may be decreased to, for example, counteract blooming. Such fine-tuning may be effected by the user or automatically as described above.

In certain embodiments, the detectors may be used to regulate the amount of illumination emitted by the illumination source(s) 220. This is particularly important as infrared energy may be harmful to humans, and while the photo bleaching properties of dyes such as ICG provide an upper limit on the energy applied to the tissue and require low dosages of wavelengths not unlike red in amounts of approximately 50 milliwatts per cm squared. Nonetheless, the perception of NIR as wavelengths which produce a substantial amount of heat is well founded. For example, detectors 33*b* and 33*a* automatically sense exposure levels of infra red energy and visible energy, respectively, and electronically communicate this information to the computer 360. Software on the computer may then compare the energy level indications received from the different detectors 33*a* and 33*b*. If the software determines that the level of infrared energy exceeds the level of visible light energy, the software may instruct the computer 360 to decrease the output of the infrared illumination source. In certain embodiments, the software may have a pre-set threshold or may allow a user to set a threshold as to an acceptable difference in energy output between different power sources. If a determination is made that the infrared detected energy exceeds the detected visible light energy by the threshold amount, the computer will then instruct the illumination source 220 to decrease output.

In some embodiment, if the software on the computer 360 determines that no infrared energy is being detected by the infrared detector, it may instruct the infrared camera to cease transmitting information to the computer or no longer use information transmitted from the infrared detector in calculations and imaging.

In some embodiments, proximal section 29 comprises an ocular member with an exit window. Such a window is useful to a physician who wishes to look through the endoscope without a camera. Proximal prisms will be provided to relay a visible image to the window, or the visible/infra red proximal prism camera invention may be used.

In certain embodiments, the physician may not wish to image in the infrared spectrum. In such embodiments, the infrared camera may be turned off, powered down or removed from the endoscope. In preferred embodiments, such turning off, powering down or removal will activate sensors or be otherwise detected by the computer, which will then send a shut off command to the infrared illumination source.

Preferably, where the aspect ratio of the prism contained within the focused beam path to the detector is defined by the exit face to the prism, the face in near proximity to the detector, and its length, as defined by the path along the optical axis, yields:

$$0.167 < D/L < 0.25$$

where:
D is defined by the diameter of the exit face, and
L is the path along the optical axis contained within the prism In certain embodiments, the proximal prism assembly is removable from the endoscope eyepiece or last optical relay member, thus requiring a focusing lens assembly that focuses the relayed light from the relay section of endoscope 260 to an external exit pupil. This focusing lens assembly is preferably color corrected to produce comparably sized images free of dominating aberrations in each of the desired color bands and corrected to compensate for the positioning of the compact proximal color splitting prism assembly. The focusing assembly must be telecentric in object space, that space between the endoscope relay and the detachable compact prism assembly first optical element. In the case of a proximal prism assembly detachable from an endoscope eyepiece the focusing lens assembly must have an external entrance pupil that maps or is positioned in close proximity to the exit pupil of the endoscope eyepiece.

In the later case an endoscope exit pupil cannot be designed much larger than the human eye pupil that views it. The mismatch between human eye pupil and endoscope exit pupil would be seen as a reduction in brightness by the user of the endoscope when used without a camera, whereas the larger the pupil the faster the f-number of the focusing lens assembly and more sensitive the system from the camera or detector's point of view.

III. Light Sources

The invention further provides a non-laser infra-red light source that can be used with endoscopes, wands, macro telephoto imagers, or any other imaging device that is capable of receiving an optical fiber. Thus, the dangers associated with lasers, such as damage to a user's or subject's retina are removed or minimized. In some embodiments, the non-laser source is part of a combined illumination source comprised of both VIS and NIR illumination. In certain other embodiments, the non-laser source is contained in a distinct housing (e.g., a light box) in optical communication with the imaging device through fiber optics.

Figure 11:
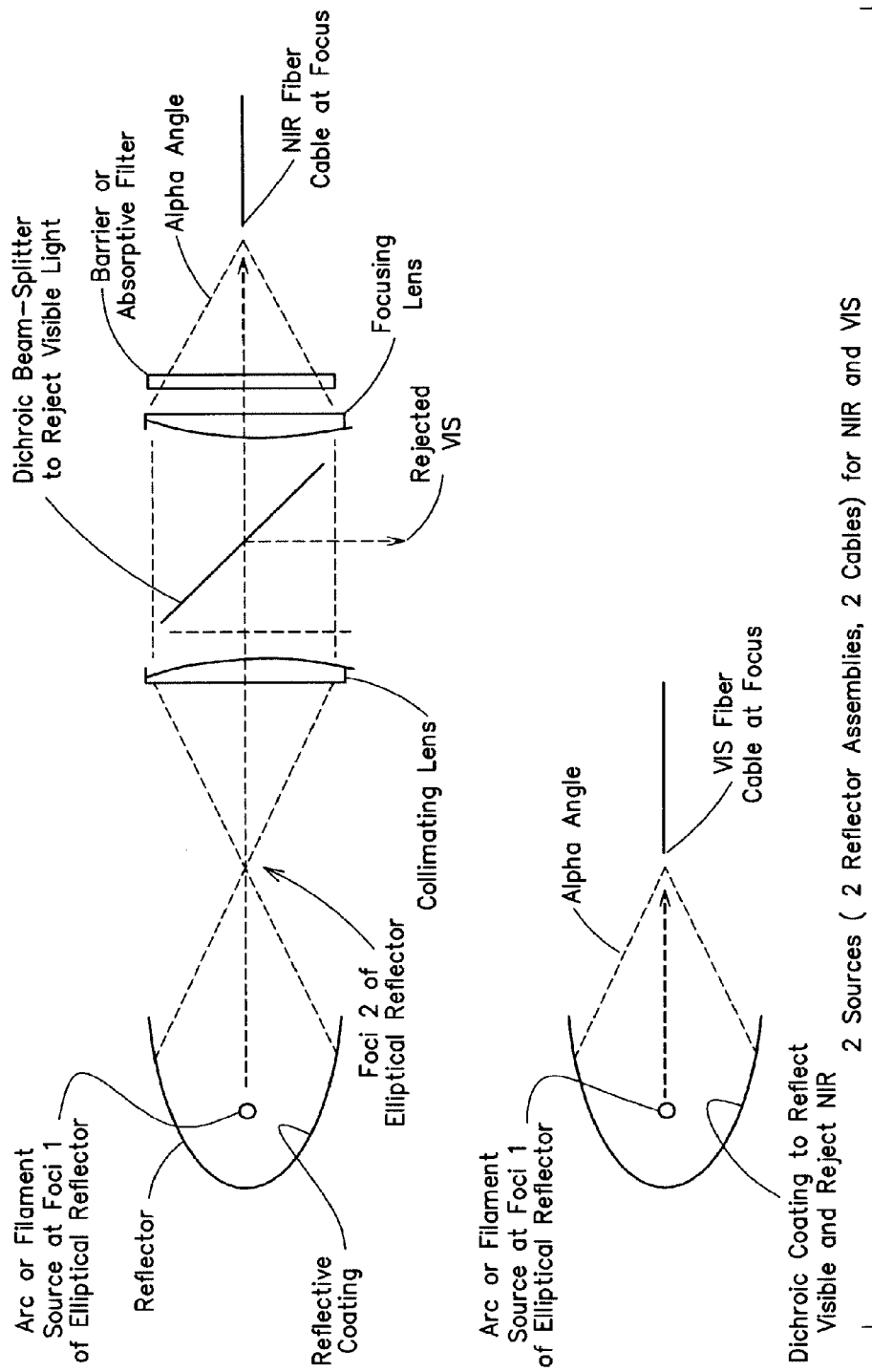
FIG. 11 illustrates a light source.

Referring now to FIG. 11, the light source includes light emitting member. Light emitting member is any light emitter that emits light energy in the infra red spectrum. Examples include tungsten halogen, xenon, and metal halide bulbs or arcs. In some embodiments, a member that emits in multiple wavelength ranges (e.g, infra red and visible) is chosen.

The light source includes an integrated reflector. Preferably, the reflector captures a significant portion of the total source power of the bulb or arc. An elliptical reflector captures a significant portion of the solid angle of the source when the reflector is positioned at one of the two foci of the ellipse, where the reflector can then redirect energy from the source arc or filament to the second foci defined by the elliptical reflector. In other embodiments, the reflector is parabolic.

The reflector has a coating that reflects infra red light to the beamsplitter that separates light of different wavelength. Infra red light from beamsplitter is then focused onto light fiber by optical assembly. The light fiber for NIR has a diameter and acceptance angle to favorably capture a substantial portion of the infra red light. Preferably, the beamsplitter routes light in the range of about 750 nm and about 800 nm to the optical assembly. In one embodiment, the numerical aperature is between about 0.4 and about 0.66. In some embodiments, the numerical aperture is between about 0.55 and about 0.66 NA. Such a combined VIS and NIR source can be used to provide illumination for endoscopes, wands, and macrotelephoto imaging devices used for NIR fluorescent imaging or combined VIS and NIR fluorescent imaging in either mono or stereo viewing mode.

In cases where the reflector is elliptical, the light member will be positioned approximately at the first foci of the ellipse, and the light fiber will be positioned approximately at the second foci which may be reimaged by a condenser lens assembly with a collimated or nearly collimated section between the said condenser lenses. Preferably, an assembly of collimating and focusing lenses is positioned between the member and the light beam splitter to collimate the light directed to beamsplitter 320. The advantage of the above configuration is the creation of near parallel paths of rays, the collimated condition, when intersecting a dichroic coating. The cut on cut off slope of such a coating is steeper if all rays are more or less parallel when interacting with the coating, therefore making it more efficient at dividing a spectrum.

In certain embodiments, the integrated reflector is parabolic. In these embodiments, the reflected light will be approximately collimated, and a collimating assembly may not be necessary to collimate the reflected light. A focusing lens or lens assembly is required to focus the energy from the source to the fiber optic cable.

Reflectors of other shapes may be used. Examples include: a reflector whose shape is modified to compensate for the aberrations of the glass envelope surrounding an arc source.

As discussed above, reflector has a coating for preferentially reflecting light in the infra red spectrum. Preferably, light at wavelengths between about 750 nm-about 820 nm is reflected. In certain embodiments, light between about 750 nm and about 800 nm is reflected. In some embodiments, light having a wavelength of between about 770 and 800 nm is reflected. In some embodiments, a coating is chosen that reflects significant amounts of light in multiple spectrums (e.g., ultraviolet, visible and/or infrared) and/or within multiple ranges within one or more of these spectrums.

In some embodiments, the coating is one of gold, silver or aluminum. Gold is particularly preferred for reflecting only wavelengths in the near infra red spectrum. Silver is particularly preferred for reflecting wavelengths in the visible and near infra red spectrums. These coatings can be preferably applied directly to the reflecting reflector 310 and are between about 1 and about 20 micrometers in thickness, and preferably between about 1 and about 10 micrometers in thickness. They can be purchased from, for example, TYDEX J.S. Co. (St. Petersburg, Russia) and vapor deposited onto the surface of interest by any number of thin film coaters in the world using vacuum deposition chambers. Gold coatings are especially preferred because they reflect well in the near IR. In some embodiments, any coating that reflects at least 80%, preferably at least 90% and most preferably at least 95% of light energy that is within the wavelengths of interest may be used. A second coating, such silicon dioxide ($SiO_2$), magnesium fluoride, silicon monoxide or a dielectric overcoat may be applied. Such coatings can be purchased from, for example, OFR, Inc., Caldwell, N.J. In some embodiments, the coating is a dichroic coating or mirror (provided by a coating supplier such as Omega Optical Inc. Brattleboro, Vt. or Chroma Technology Corp., Rockingham, Vt.) A coating of gold, silver or aluminum is preferred over dichroic coatings for efficiency since they are angle sensitive and such coatings could, over the collecting surface of the reflector, vary in efficiency.

Referring now to the beamsplitter, it routes energy in the infra red spectrum to light fiber. The light energy routed to light fiber is within the spectrum desired for imaging. In other words, if the dye being used is ICG, the beamsplitter will direct light to the light guide that is capable of exciting the ICG. For example, it may have a wavelength between about 750-about 820 nm, and more preferably between about 750 nm and 800 nm, or between about 770 nm and about 800 nm. The beam splitter may be an optical plate coated with, or cube containing a dichroic coating or interference filter such as a high/low index pair coating described above in relation to the endoscope relay section. The configuration of such an interference filter varies from transmission filters in selection and placement of high/low index pairs to optimize blockage and spectral width. In some embodiments, the beamsplitter assembly may require an absorptive filter that absorbs light rays that are at a wavelength above or below the wavelengths of interest. If the energy is sufficiently intense there may be excess heating that can be ameliorated with the addition of a fan.

Figure 12:
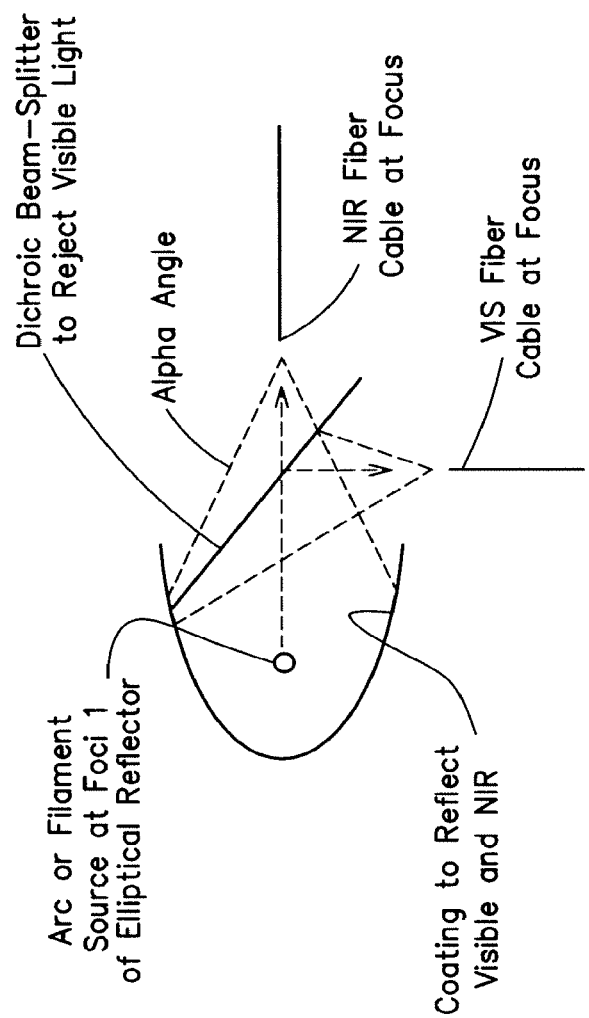
FIG. 12 illustrates a second embodiment of the light source.

FIG. 12 shows another embodiment of the light source. It is similar to the previously described light source except that the light member includes a second optical fiber that provides light at different wavelengths than the first optical fiber. Thus, it can be used for multimodal imaging (e.g., simultaneous imaging in the infra red spectrum and also imaging in the visible spectrum). In this embodiment, light emitting member is chosen such that it produces light both in the infra red and in the second desired range. Preferably, the second range is within the visible spectrum of about 400 nm to about 700 nm. Reflector includes a coating that reflects light in both the infra red and in the second desired range, e.g., silver. The beam splitter than routes light within the second desired range to second light fiber.

In some embodiments, additional absorptive filters may be placed between beamsplitter and one or more of the first and second light fibers to further reduce unwanted energy. Locating these filters in this position has several advantages. The first is; there is physically more room than the earlier case where the absorbing filters were located between the first and second foci of the elliptical reflector. The second advantage is also associated with more space, as the beam diameter may be larger than in the converging beam path between the two foci. This results in less flux density on the filter and less substrate heating in the filter. Thirdly, more room results in freedom to use more filters of differing configurations. Fourthly, more room permits the use of thicker more efficient absorptive filters.

In certain embodiments, the alpha angle of the light emitting member, the reflector and focusing lens in a one-dimensional direction satisfy the condition of 0.42 for the ratio of D/L<tan alpha<1.4D/L where alpha is the angle of the marginal ray and where D is one half of the effective diameter of the reflector adjacent to the light emitting member 300 or focusing lens to insert energy from light emitting member 300 to the light fiber and L is the distance from the limiting aperture of either the reflector or focusing lens.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

The invention claimed is:

1. An elongated lens system in an endoscope or wand for fluorescence and visible light imaging, comprising:
    a first lens group comprising an objective assembly;
    a second lens group comprising a relay lens group; and
    an ocular lens group,
    wherein the relay lens group comprises a plurality of light transmitting members each comprising a transmitting glass surface facing an air space and an optical coating on the transmitting glass surface, wherein each coated light transmitting member is configured to reflect between 0.5% and 5% of first and second wavelengths of interest, wherein the first wavelength of interest is in the infrared spectrum and the second wavelength of interest is in the visible spectrum.

2. The elongated lens system of claim 1, where the relay lens group comprises at least 30 air glass surfaces.

3. The elongated lens system of claim 1, wherein the first wavelength of interest is between 825 nm and 835 nm.

4. The elongated lens system of claim 1, wherein the plurality of light transmitting members comprise glasses with an index of refraction ranging from 1.5 to 1.65.

5. The elongated lens system of claim 1, wherein the plurality of light transmitting members comprise glasses with an index of refraction ranging from 1.65 to 1.7.

6. The elongated lens system of claim 1, further comprising a filter configured to block light at an excitation wavelength.

7. The elongated lens system of claim 1, wherein the optical coating comprises layers of a high index coating material and a low index coating material.

8. The elongated lens system of claim 1, wherein the optical coating comprises layers of $TiO_2$ and $MgF_2$.

9. The elongated lens system of claim 1, wherein the optical coating comprises layers of $TiO_2$ and $SiO_2$.

10. The elongated lens system of claim 1, wherein the optical coating comprises layers of $ZrO_2$ and $MgF_2$.

11. The elongated lens system of claim 1, wherein the optical coating comprises layers of $Ta_2O_5$ and $SiO_2$.

* * * * *

UNITED STATES PATENT AND TRADEMARK OFFICE
CERTIFICATE OF CORRECTION

PATENT NO. : 9,877,654 B2  
APPLICATION NO. : 13/585824  
DATED : January 30, 2018  
INVENTOR(S) : John C. Tesar Page 1 of 1

It is certified that error appears in the above-identified patent and that said Letters Patent is hereby corrected as shown below:

On the Title Page

Item (73) Assignee, please replace:
"NOVADAQ TECHNOLOGIES INC."

With:
--NOVADAQ TECHNOLOGIES ULC--

Signed and Sealed this
Twentieth Day of February, 2018

Andrei Iancu
*Director of the United States Patent and Trademark Office*